United States Patent
Kanuma et al.

(10) Patent No.: US 8,461,182 B2
(45) Date of Patent: Jun. 11, 2013

(54) 7-PIPERIDINOALKYL-3, 4-DIHYDROQUINOLONE DERIVATIVE

(75) Inventors: Kosuke Kanuma, Toshima-ku (JP); Naoki Miyakoshi, Toshima-ku (JP); Madoka Kawamura, Toshima-ku (JP); Tsuyoshi Shibata, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 67 days.

(21) Appl. No.: 13/122,281

(22) PCT Filed: Sep. 30, 2009

(86) PCT No.: PCT/JP2009/067441
§ 371 (c)(1),
(2), (4) Date: Apr. 1, 2011

(87) PCT Pub. No.: WO2010/038901
PCT Pub. Date: Apr. 8, 2010

(65) Prior Publication Data
US 2011/0178304 A1    Jul. 21, 2011

(30) Foreign Application Priority Data
Oct. 2, 2008 (JP) .................... 2008-257072

(51) Int. Cl.
*A61K 31/04*    (2006.01)
*C07D 215/38*    (2006.01)

(52) U.S. Cl.
USPC ........................................ 514/312; 546/159

(58) Field of Classification Search
USPC .......................................... 546/159; 514/312
See application file for complete search history.

(56) References Cited

U.S. PATENT DOCUMENTS

| | | |
|---|---|---|
| 2005/0197350 A1 | 9/2005 | Sekiguchi et al. |
| 2005/0209274 A1* | 9/2005 | Lynch et al. .................. 514/312 |
| 2007/0010671 A1 | 1/2007 | Sekiguchi et al. |
| 2007/0037836 A1 | 2/2007 | Sekiguchi et al. |
| 2008/0090863 A1 | 4/2008 | Sekiguchi et al. |
| 2009/0036448 A1 | 2/2009 | Sekiguchi et al. |
| 2010/0081825 A1 | 4/2010 | Sekiguchi et al. |

FOREIGN PATENT DOCUMENTS

WO    2008/044632 A1    4/2008

OTHER PUBLICATIONS

Iyengar, Bio & MEd CHem Lett, vol. 17, pp. 874-878, 2007.*

Rajesh R. Iyengar, et al., "An evaluation of 3, 4-methylenedioxy phenyl replacements in the aminopiperidine chromone class of MCHr1 antagonists", Bioorganic & Medicinal Chemistry Letters, 2007, pp. 874-878, vol. 17, No. 4.

Yumiko Saito, et al., "Melanin-concentrating Hormone Receptor: An Orphan Receptor Fits the Key", Trends Endocrinol Metab, 2000, pp. 299-303, vol. 11, No. 8.

Shigeyuki Chaki, et al. "Melanin-Concentrating Hormone Receptor 1 Antagonists for the Treatment of Depression and Anxiety", Drug Development Research, 2005, pp. 278-290, vol. 65.

Book of Abstracts, 224th the American Chemical Society Medi-343, Boston, MA., Aug. 18-22, 2002, 2 pages.

Nick Kim, et al., "Identification of substituted 4-aminopiperidines and 3-aminopyrrolidines as potent MCH-R1 antagonists for the treatment of obesity", Bioorganic & Medicinal Chemistry Letters, 2006, pp. 5445-5450, vol. 16.

Anil Vasudevan, et al., "Identification of aminopiperidine benzamides as MCHr1 antagonists", Bioorganic & Medicinal Chemistry Letters, 2005, pp. 3412-3416, vol. 15.

* cited by examiner

*Primary Examiner* — D M Seaman
(74) *Attorney, Agent, or Firm* — Sughrue Mion, PLLC

(57) ABSTRACT

PROBLEM
To provide a novel compound, a pharmaceutically acceptable salt or a hydrate thereof useful for preventing or treating for depression, anxiety disorders (such as generalized anxiety disorder, posttraumatic stress disorder, panic disorder, obsessive-compulsive disorder or social anxiety disorder), attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder (such as Parkinson's disease, epilepsy, convulsion or tremor), drug abuse, drug addiction or sexual dysfunction, based on a melanin-concentrating hormone receptor (MCH receptor) antagonistic action.

SOLUTION
A compound, a pharmaceutically acceptable salt or a hydrate thereof represented by the formula (I).

[Formula (I)]

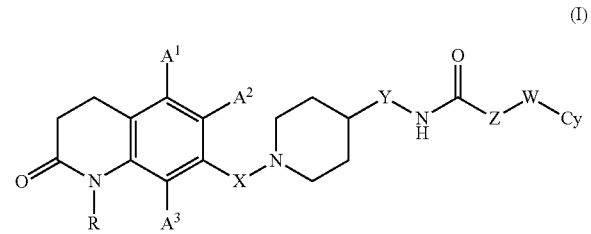

7 Claims, No Drawings

7-PIPERIDINOALKYL-3, 4-DIHYDROQUINOLONE DERIVATIVE

CROSS REFERENCE TO RELATED APPLICATIONS

This is a National Stage of International Application No. PCT/JP2009/067441 filed Sep. 30, 2009, claiming priority based on Japanese Patent Application No. 2008-257072 filed Oct. 2, 2008, the contents of all of which are incorporated herein by reference in their entirety.

TECHNICAL FIELD

The present invention relates to a compound having a melanin-concentrating hormone receptor antagonistic effect, a pharmaceutically acceptable salt or a hydrate thereof.

BACKGROUND ART

Depression and anxiety disorders constitute main psychiatric diseases. It is assumed that the lifetime prevalence of depression and anxiety disorders has been steadily increased in recent years. To date, tricyclic antidepressants (TCA), selective serotonin reuptake inhibitors (SSRI), serotonin and noradrenaline reuptake inhibitors (SNRI) and the like based on the monoamine hypothesis have been developed as antidepressants. Benzodiazepines based on the γ-aminobutyric acid mechanism (GABA) have been used as anxiolytics. In recent years, SSRI and SNRI have been demonstrated to be also effective for anxiety disorders such as panic disorder and obsessive-compulsive disorder for which benzodiazepines are not effective, and they are also the first-line treatments for anxiety disorders. However, SSRI and SNRI are not effective in patients with treatment-refractory depression and need to be taken for several weeks for the onset of antidepressive and anxiolytic effects, for example, disadvantageously. Accordingly, it is desirable to develop an antidepressant and anxiolytic based on a mechanism of action differing from that of an existing drug.

Melanin-concentrating hormone (MCH), a neuropeptide, consisting of 19 amino acids is biosynthesized and widely distributed in the limbic system and the like in the brain. The melanin-concentrating hormone-1 receptor (MCH1R) and the melanin-concentrating hormone-2 receptor (MCH2R) have been already known as two MCH receptor subtypes. MCH2R is not expressed in rodents and its physiological functions have not yet been elucidated; however, it has been elucidated that MCH1R is deeply associated with eating behavior and energy metabolism. More specifically, there is a report that food intake increases by injection of MCH to a rat. There is another report that a decrease of body-weight and an increase of metabolism are observed in MCH-defective gene-modified mice (see NON-PATENT DOCUMENT 1). Accordingly, an MCH1R antagonist may be possibly used as a prophylactic or therapeutic drug for obesity, eating disorder, appetite disorder, hyperphagia, bulimia, cibophobia, etc.

On the other hand, it is reported that MCH1R is also deeply involved in regulation of stress response and emotion. Activation of the hypothalamus-pituitary-adrenal (HPA) axis by MCH is antagonized by an MCH1R antagonist and a neutralizing antibody against corticotropin-releasing factor (CRF). MCH is presumed to activate the HPA system through facilitation of release of CRF from the hypothalamus. MCH1R is predominantly distributed in the accumbens involved in motivation and reward. When MCH is injected into this site, depressive-like symptoms are observed in a forced swimming test, whereas MCH knockout mice have antidepressive-like symptoms. A study using MCH1R knockout mice shows that MCH1R negatively regulates the activity of dopaminergic neurons involved in reward in the accumbens. Moreover, ATC0175, a nonpeptidic MCH1R antagonist, has antidepressive-like and anxiolytic-like effects in experimental animal models (NON-PATENT DOCUMENT 2). From the above facts, it is suggested that MCH1R is involved not only in control of eating behavior and energy metabolism but also in onset of depression and anxiety, and it can be expected that an MCH receptor antagonist, in particular, an MCH1R antagonist, may be an antidepressant and anxiolytic having a mechanism of action differing from that of a conventional one.

Recently, MCH receptor antagonists having a naphthalene skeleton and a 1,3-benzodioxole skeleton are disclosed in PATENT DOCUMENT 1 and NON-PATENT DOCUMENTs 3, 4, 5 and 6. However, these documents neither disclose nor suggest the structure of a compound according to the present invention.

PATENT DOCUMENT 1: U.S. Patent Application Publication No. 2005/209274
NON-PATENT DOCUMENT 1: Trends Endocrinol Metab vol. 11, p. 299-303 (2000)
NON-PATENT DOCUMENT 2: Drug Development Research vol. 65, p. 278-290 (2005)
NON-PATENT DOCUMENT 3: 224th The American Chemical Society MEDI-343 (2002)
NON-PATENT DOCUMENT 4: Bioorganic & Medicinal Chemistry Letters vol. 16, p. 5445-5450 (2006)
NON-PATENT DOCUMENT 5: Bioorganic & Medicinal Chemistry Letters vol. 15, p. 3412-3416 (2005)
NON-PATENT DOCUMENT 6: Bioorganic & Medicinal Chemistry Letters vol. 17, p. 874-878 (2007)

DISCLOSURE OF THE INVENTION

Problems to be Solved by the Invention

An object of the present invention is to provide a novel compound useful for preventing or treating a disease such as depression, anxiety disorders (such as generalized anxiety disorder, posttraumatic stress disorder, panic disorder, obsessive-compulsive disorder or social anxiety disorder), attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder (such as Parkinson's disease, epilepsy, convulsion or tremor), drug abuse, drug addiction or sexual dysfunction, based on an MCH receptor antagonistic effect, a pharmaceutically acceptable salt or a hydrate thereof.

Means for Solving the Problems

As the result that the present inventors have conducted intensive studies, they found that a 7-piperidinoalkyl-3,4-dihydroquinolone compound represented by the following formula (I) has excellent MCH receptor antagonistic action. Based on the finding, the present invention was accomplished.

More specifically, the present invention provides,
1) A compound represented by formula (I), a pharmaceutically acceptable salt or a hydrate thereof:

[Formula 1]

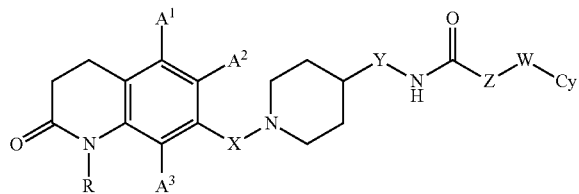

(I)

wherein, in the formula (I)

R is a hydrogen atom or a $C_{1-6}$ alkyl group;

$A^1$, $A^2$ and $A^3$, which may be the same or different, are each a hydrogen atom, a halogen atom, a $C_{1-6}$ alkyl group or a $C_{1-6}$ alkoxy group;

X is a $C_{1-6}$ alkylene group;

Y is a bond or a $C_{1-6}$ alkylene group;

Z is a bond or a $C_{1-6}$ alkylene group, wherein the $C_{1-6}$ alkylene group may be substituted with an aryl group;

W is a bond or an oxygen atom; and

Cy is an aryl group or a heteroaryl group, wherein the aryl group or the heteroaryl group may have one to three substituents, which may be the same or different, selected from the group consisting of a halogen atom, a cyano group, a $C_{1-6}$ alkyl group, a $C_{1-6}$ alkoxy group, wherein the $C_{1-6}$ alkyl group or the $C_{1-6}$ alkoxy group may be substituted with one to three halogen atoms, and a $C_{2-6}$ alkanoyl group;

2) The compound, a pharmaceutically acceptable salt or a hydrate thereof according to the above 1), in which, in the formula (I)

R is a hydrogen atom;

$A^1$, $A^2$ and $A^3$ are each a hydrogen atom;

X is a $C_{1-6}$ alkylene group;

Y is a bond;

Z is a bond or a $C_{1-6}$ alkylene group, wherein the $C_{1-6}$ alkylene group may be substituted with an aryl group;

W is a bond or an oxygen atom; and

Cy is a phenyl group or a pyridyl group, wherein the phenyl group or the pyridyl group may have one to three substituents, which may be the same or different, selected from the group consisting of a halogen atom, a cyano group, a $C_{1-6}$ alkyl group, a $C_{1-6}$ alkoxy group, wherein the $C_{1-6}$ alkyl group or the $C_{1-6}$ alkoxy group may be substituted with one to three halogen atoms, and a $C_{2-6}$ alkanoyl group;

3) The compound, a pharmaceutically acceptable salt or a hydrate thereof according to the above 1), in which, in the formula (I), R is a hydrogen atom;

$A^1$, $A^2$ and $A^3$ are each a hydrogen atom;

X is a methylene group, wherein the methylene group may be substituted with a methyl group;

Y is a bond;

Z is a bond or a methylene group;

W is a bond or an oxygen atom; and

Cy is a phenyl group, wherein the phenyl group may have one to three substituents, which may be the same or different, selected from the group consisting of a halogen atom, a $C_{1-6}$ alkyl group, a $C_{1-6}$ alkoxy group and a $C_{2-6}$ alkanoyl group;

4) The compound, a pharmaceutically acceptable salt or a hydrate thereof according to the above 1), wherein the compound represented by the formula (I) is 3-methoxy-N-{1-[(2-oxo-1,2,3,4-tetrahydroquinolin-7-yl)methyl]piperidin-4-yl}benzamide, 3-fluoro-N-{1-[(2-oxo-1,2,3,4-tetrahydroquinolin-7-yl)methyl]piperidin-4-yl}benzamide, 3,5-difluoro-N-{1-[(2-oxo-1,2,3,4-tetrahydroquinolin-7-yl)methyl]piperidin-4-yl}benzamide, 3,4-difluoro-N-{1-[(2-oxo-1,2,3,4-tetrahydroquinolin-7-yl)methyl]piperidin-4-yl}benzamide, 4-fluoro-N-{1-[(2-oxo-1,2,3,4-tetrahydroquinolin-7-yl)methyl]piperidin-4-yl}benzamide, 3-chloro-N-{1-[(2-oxo-1,2,3,4-tetrahydroquinolin-7-yl)methyl]piperidin-4-yl}benzamide, 3-methyl-N-{1-[(2-oxo-1,2,3,4-tetrahydroquinolin-7-yl)methyl]piperidin-4-yl}benzamide, 3,5-dichloro-N-{1-[(2-oxo-1,2,3,4-tetrahydroquinolin-7-yl)methyl]piperidin-4-yl}benzamide, 3,4-dichloro-N-{1-[(2-oxo-1,2,3,4-tetrahydroquinolin-7-yl)methyl]piperidin-4-yl}benzamide, 4-fluoro-3-methyl-N-{1-[(2-oxo-1,2,3,4-tetrahydroquinolin-7-yl)methyl]piperidin-4-yl}benzamide, 4-fluoro-N-{1-[(2-oxo-1,2,3,4-tetrahydroquinolin-7-yl)methyl]piperidin-4-yl}-3-(trifluoromethyl)benzamide, 3-fluoro-N-{1-[(2-oxo-1,2,3,4-tetrahydroquinolin-7-yl)methyl]piperidin-4-yl}-5-(trifluoromethyl)benzamide, 3,5-dimethoxy-N-{1-[(2-oxo-1,2,3,4-tetrahydroquinolin-7-yl)methyl]piperidin-4-yl}benzamide, N-{1-[(2-oxo-1,2,3,4-tetrahydroquinolin-7-yl)methyl]piperidin-4-yl}benzamide, N-{1-[(2-oxo-1,2,3,4-tetrahydroquinolin-7-yl)methyl]piperidin-4-yl}-2,2-diphenylacetamide, 4-chloro-3-fluoro-N-{1-[(2-oxo-1,2,3,4-tetrahydroquinolin-7-yl)methyl]piperidin-4-yl}benzamide, 3-bromo-N-{1-[(2-oxo-1,2,3,4-tetrahydroquinolin-7-yl)methyl]piperidin-4-yl}benzamide, 3-fluoro-5-methoxy-N-{1-[(2-oxo-1,2,3,4-tetrahydroquinolin-7-yl)methyl]piperidin-4-yl}benzamide, 3-chloro-4-fluoro-N-{1-[(2-oxo-1,2,3,4-tetrahydroquinolin-7-yl)methyl]piperidin-4-yl}benzamide, 3-acetyl-N-{1-[(2-oxo-1,2,3,4-tetrahydroquinolin-7-yl)methyl]piperidin-4-yl}benzamide, 3,4,5-trifluoro-N-{1-[(2-oxo-1,2,3,4-tetrahydroquinolin-7-yl)methyl]piperidin-4-yl}benzamide, 4-fluoro-3-methoxy-N-{1-[(2-oxo-1,2,3,4-tetrahydroquinolin-7-yl)methyl]piperidin-4-yl}benzamide, 3-chloro-5-fluoro-N-{1-[(2-oxo-1,2,3,4-tetrahydroquinolin-7-yl)methyl]piperidin-4-yl}benzamide, 3-cyano-N-{1-[(2-oxo-1,2,3,4-tetrahydroquinolin-7-yl)methyl]piperidin-4-yl}benzamide, 5-chloro-N-{1-[(2-oxo-1,2,3,4-tetrahydroquinolin-7-yl)methyl]piperidin-4-yl}pyridine-3-carboxamide, 3-chloro-5-methoxy-N-{1-[(2-oxo-1,2,3,4-tetrahydroquinolin-7-yl)methyl]piperidin-4-yl}benzamide, 4-chloro-3-methyl-N-{1-[(2-oxo-1,2,3,4-tetrahydroquinolin-7-yl)methyl]piperidin-4-yl}benzamide, 2-(3-chloro-4-fluorophenoxy)-N-{1-[(2-oxo-1,2,3,4-tetrahydroquinolin-7-yl)methyl]piperidin-4-yl}acetamide, 2-(3-chlorophenoxy)-N-{1-[(2-oxo-1,2,3,4-tetrahydroquinolin-7-yl)methyl]piperidin-4-yl}acetamide, 3-chloro-4-fluoro-N-{1-[1-(2-oxo-1,2,3,4-tetrahydroquinolin-7-yl)ethyl]piperidin-4-yl}benzamide or N-{1-[(6-fluoro-2-oxo-1,2,3,4-tetrahydroquinolin-7-yl)methyl]piperidin-4-yl}-3-methoxybenzamide;

5) A pharmaceutical composition containing the compound, a pharmaceutically acceptable salt or a hydrate thereof according to any one of the above 1) to 4) as an active ingredient;

6) The pharmaceutical composition according to the above 5), which is a melanin-concentrating hormone receptor antagonist; and 7) A prophylactic or therapeutic drug containing the compound, a pharmaceutically acceptable salt or a hydrate thereof according to any one of the above 1) to 4), as an active ingredient, for depression, anxiety disorders, attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder, drug abuse, drug addiction or sexual dysfunction.

Advantages of the Invention

The compound of the present invention was found to have an MCH receptor antagonistic activity. A medicinal drug containing the compound of the present invention is useful as a prophylactic or therapeutic drug for depression, anxiety disorders (such as generalized anxiety disorder, posttraumatic stress disorder, panic disorder, obsessive-compulsive disorder or social anxiety disorder), attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder (such as Parkinson's disease, epilepsy, convulsion or tremor), drug abuse, drug addiction or sexual dysfunction, based on the MCH receptor antagonistic action.

BEST MODE FOR CARRYING OUT THE INVENTION

The terms used in this specification are as defined as follows.

The "halogen atom" represents a fluorine atom, a chlorine atom, a bromine atom and an iodine atom.

The "$C_{1-6}$ alkyl group" represents a straight chain alkyl group having 1 to 6 carbon atoms or a branched chain alkyl group having 3 to 6 carbon atoms. The straight chain alkyl group represents a methyl group, an ethyl group, a propyl group, a butyl group, a pentyl group and a hexyl group. The branched chain alkyl group represents, for example, an isopropyl group, an isobutyl group, a tert-butyl group, an isopentyl group, a 1-ethylpropyl group, and an isohexyl group.

The "$C_{1-6}$ alkoxy group" represents a straight chain alkoxy group having 1 to 6 carbon atoms or a branched chain alkoxy group having 3 to 6 carbon atoms. The straight chain alkoxy group represents a methoxy group, an ethoxy group, a propoxy group, a butoxy group, a pentyloxy group and a hexyloxy group. The branched chain alkoxy group represents, for example, an isopropoxy group, an isobutoxy group, a tert-butoxy group, an isopentyloxy group, a 1-ethylpropoxy group and an isohexyloxy group.

The "$C_{1-6}$ alkylene group" represents a straight chain alkylene group having 1 to 6 carbon atoms or a branched chain alkylene group having 3 to 6 carbon atoms, for example, including a methylene group, an ethylene group, a propylene group, a butylene group, a pentylene group, a hexylene group, an isopropylene group, an isobutylene group, a tert-butylene group, an isopentylene group, a 1-ethylpropylene group and an isohexylene group etc.

The "$C_{2-6}$ alkanoyl group" represents a carbonyl group having a $C_{1-5}$ alkyl group. Examples thereof include a methylcarbonyl group, an ethylcarbonyl group, a propylcarbonyl group, a butylcarbonyl group, a pentylcarbonyl group, a hexylcarbonyl group, an isopropylcarbonyl group, an isobutylcarbonyl group, a tert-butylcarbonyl group, an isopentylcarbonyl group, 1-ethylpropylcarbonyl group and an isohexylcarbonyl group.

The "aryl group" represents monocyclic to tetracyclic aromatic carbocyclic groups formed of 6 to 18 carbon atoms. Examples thereof include a phenyl group, a naphthyl group, an anthracenyl group and a 9H-fluorenyl group.

The "heteroaryl group" represents monocyclic to bicyclic aromatic heterocyclic groups formed of 5 to 10 atoms including 1 to 3 hetero atoms selected from a nitrogen atom, an oxygen atom and a sulfur atom, other than carbon atoms. Examples thereof include a pyrrolyl group, a pyrazolyl group, an imidazolyl group, a furyl group, an oxazolyl group, an isoxazolyl group, a thienyl group, a thiazolyl group, an isothiazolyl group, a pyridyl group, a pyrimidinyl group, a pyridazinyl group, a pyrazinyl group, an indolyl group, a benzofuryl group, a benzothienyl group, a benzimidazolyl group, a benzoxazolyl group, a benzothiazolyl group, a benzopyrazolyl group, a benzoisoxazolyl group, a benzoisothiazolyl group, a quinolyl group, a isoquinolyl group, a quinazolinyl group, a quinoxalinyl group, a phthalazinyl group, a chinolinyl group and a 9H-xanthenyl group.

An aspect of the compound of the present invention relates to a 7-piperidinoalkyl-3,4-dihydroquinolone compound, a pharmaceutically acceptable salt or a hydrate thereof represented by the formula (I):

[Formula 2]

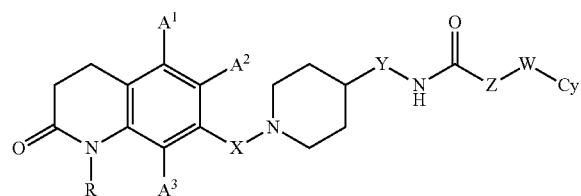

(I)

{where (in the formula (I)), R, X, Y, Z, W, $A^1$, $A^2$, $A^3$ and Cy are the same as defined above}.

A preferable aspect of the compound of the present invention is as follows. In the formula (I), R is a hydrogen atom, $A^1$, $A^2$ and $A^3$ each represent a hydrogen atom, X is a $C_{1-6}$ alkylene group, Y is a bond, Z is a bond or a $C_{1-6}$ alkylene group (where the $C_{1-6}$ alkylene group may be substituted with an aryl group), W is a bond or an oxygen atom, and Cy is a phenyl group or a pyridyl group (where the phenyl group or the pyridyl group may have one to three substituents, which may be the same or different, selected from the group consisting of a halogen atom, a cyano group, a $C_{1-6}$ alkyl group, a $C_{1-6}$ alkoxy group, wherein the $C_{1-6}$ alkyl group or the $C_{1-6}$ alkoxy group may be substituted with one to three halogen atoms, and a $C_{2-6}$ alkanoyl group).

Another preferable aspect of the compound of the present invention is as follows. In the formula (I), R is a hydrogen atom, $A^1$, $A^2$ and $A^3$ are each a hydrogen atom, X is a methylene group (where the methylene group may be substituted with a methyl group), Y is a bond, Z is a bond or a methylene group, W is a bond or an oxygen atom, and Cy is a phenyl group (where the phenyl group may have one to three substituents, which may be the same or different, selected from the group consisting of a halogen atom, a $C_{1-6}$ alkyl group, a $C_{1-6}$ alkoxy group and a $C_{2-6}$ alkanoyl group). The above phenyl group is preferably an unsubstituted phenyl group or a substituted phenyl group represented by any one of the formulas (IIa) to (IId):

[Formula 3]

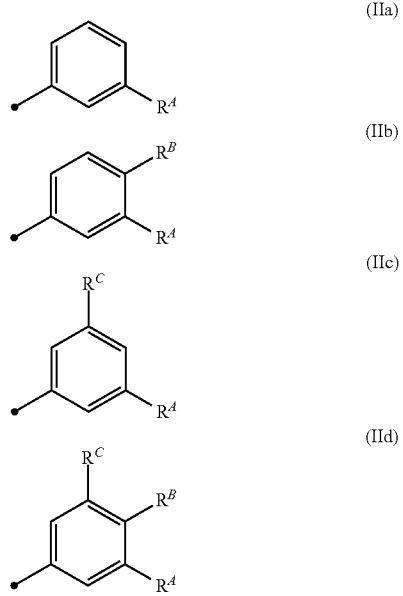

{where $R^A$, $R^B$ and $R^C$, which may be the same or different, each represent a halogen atom, a $C_{1-6}$ alkyl group, a $C_{1-6}$ alkoxy group or a $C_{2-6}$ alkanoyl group}.

A preferred specific compound of the present invention is
3-methoxy-N-{1-[(2-oxo-1,2,3,4-tetrahydroquinolin-7-yl) methyl]piperidin-4-yl}benzamide,
3-fluoro-N-{1-[(2-oxo-1,2,3,4-tetrahydroquinolin-7-yl)methyl]piperidin-4-yl}benzamide,
3,5-difluoro-N-{1-[(2-oxo-1,2,3,4-tetrahydroquinolin-7-yl) methyl]piperidin-4-yl}benzamide,
3,4-difluoro-N-{1-[(2-oxo-1,2,3,4-tetrahydroquinolin-7-yl) methyl]piperidin-4-yl}benzamide,
4-fluoro-N-{1-[(2-oxo-1,2,3,4-tetrahydroquinolin-7-yl)methyl]piperidin-4-yl}benzamide,
3-chloro-N-{1-[(2-oxo-1,2,3,4-tetrahydroquinolin-7-yl)methyl]piperidin-4-yl}benzamide,
3-methyl-N-{1-[(2-oxo-1,2,3,4-tetrahydroquinolin-7-yl)methyl]piperidin-4-yl}benzamide,
3,5-dichloro-N-{1-[(2-oxo-1,2,3,4-tetrahydroquinolin-7-yl) methyl]piperidin-4-yl}benzamide,
3,4-dichloro-N-{1-[(2-oxo-1,2,3,4-tetrahydroquinolin-7-yl) methyl]piperidin-4-yl}benzamide,
4-fluoro-3-methyl-N-{1-[(2-oxo-1,2,3,4-tetrahydroquinolin-7-yl)methyl]piperidin-4-yl}benzamide,
4-fluoro-N-{1-[(2-oxo-1,2,3,4-tetrahydroquinolin-7-yl)methyl]piperidin-4-yl}-3-(trifluoromethyl)benzamide,
3-fluoro-N-{1-[(2-oxo-1,2,3,4-tetrahydroquinolin-7-yl)methyl]piperidin-4-yl}-5-(trifluoromethyl)benzamide,
3,5-dimethoxy-N-{1-[(2-oxo-1,2,3,4-tetrahydroquinolin-7-yl)methyl]piperidin-4-yl}benzamide,
N-{1-[(2-oxo-1,2,3,4-tetrahydroquinolin-7-yl)methyl]piperidin-4-yl}benzamide,
N-{1-[(2-oxo-1,2,3,4-tetrahydroquinolin-7-yl)methyl]piperidin-4-yl}-2,2-diphenylacetamide,
4-chloro-3-fluoro-N-{1-[(2-oxo-1,2,3,4-tetrahydroquinolin-7-yl)methyl]piperidin-4-yl}benzamide,
3-bromo-N-{1-[(2-oxo-1,2,3,4-tetrahydroquinolin-7-yl)methyl]piperidin-4-yl}benzamide,
3-fluoro-5-methoxy-N-{1-[(2-oxo-1,2,3,4-tetrahydroquinolin-7-yl)methyl]piperidin-4-yl}benzamide,
3-chloro-4-fluoro-N-{1-[(2-oxo-1,2,3,4-tetrahydroquinolin-7-yl)methyl]piperidin-4-yl}benzamide,
3-acetyl-N-{1-[(2-oxo-1,2,3,4-tetrahydroquinolin-7-yl)methyl]piperidin-4-yl}benzamide,
3,4,5-trifluoro-N-{1-[(2-oxo-1,2,3,4-tetrahydroquinolin-7-yl)methyl]piperidin-4-yl}benzamide,
4-fluoro-3-methoxy-N-{1-[(2-oxo-1,2,3,4-tetrahydroquinolin-7-yl)methyl]piperidin-4-yl}benzamide,
3-chloro-5-fluoro-N-{1-[(2-oxo-1,2,3,4-tetrahydroquinolin-7-yl)methyl]piperidin-4-yl}benzamide,
3-cyano-N-{1-[(2-oxo-1,2,3,4-tetrahydroquinolin-7-yl)methyl]piperidin-4-yl}benzamide,
5-chloro-N-{1-[(2-oxo-1,2,3,4-tetrahydroquinolin-7-yl)methyl]piperidin-4-yl}pyridine-3-carboxamide,
3-chloro-5-methoxy-N-{1-[(2-oxo-1,2,3,4-tetrahydroquinolin-7-yl)methyl]piperidin-4-yl}benzamide,
4-chloro-3-methyl-N-{1-[(2-oxo-1,2,3,4-tetrahydroquinolin-7-yl)methyl]piperidin-4-yl}benzamide,
2-(3-chloro-4-fluorophenoxy)-N-{1-[(2-oxo-1,2,3,4-tetrahydroquinolin-7-yl)methyl]piperidin-4-yl}acetamide,
2-(3-chlorophenoxy)-N-{1-[(2-oxo-1,2,3,4-tetrahydroquinolin-7-yl)methyl]piperidin-4-yl}acetamide,
3-chloro-4-fluoro-N-{1-[1-(2-oxo-1,2,3,4-tetrahydroquinolin-7-yl)ethyl]piperidin-4-yl}benzamide,
N-{1-[(6-fluoro-2-oxo-1,2,3,4-tetrahydroquinolin-7-yl)methyl]piperidin-4-yl}-3-methoxybenzamide,
a pharmaceutically acceptable salt or a hydrate thereof.

An aspect of the compound of the present invention is a medical drug containing at least one of the compounds or pharmaceutically acceptable salts thereof described in this specification, as an active ingredient.

An aspect of the compound of the present invention is a medical drug containing at least one of the compounds or pharmaceutically acceptable salts thereof serving as an MCH receptor antagonist described in this specification, as an active ingredient.

An aspect of the compound of the present invention is a prophylactic or therapeutic drug containing at least one of the compounds, pharmaceutically acceptable salts or hydrates thereof described in this specification, as an active ingredient, for depression, anxiety disorders (such as generalized anxiety disorder, posttraumatic stress disorder, panic disorder, obsessive-compulsive disorder or social anxiety disorder), attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder (such as Parkinson's disease, epilepsy, convulsion or tremor), drug abuse, drug addiction or sexual dysfunction. A preferable aspect is a prophylactic or therapeutic drug containing at least one of the compounds, pharmaceutically acceptable salts or hydrates thereof described in this specification, as an active ingredient, for depression and anxiety disorders. As another preferable aspect is a prophylactic or therapeutic drug containing at least one of the compounds, pharmaceutically acceptable salts or hydrates thereof described in this specification, as an active ingredient, for obesity, eating disorder, appetite disorder, hyperphagia, bulimia and cibophobia.

A preferable compound of the present invention has excellent MCH receptor antagonistic action; however, has low binding affinity to an hERG channel. The compound having strong binding affinity to the hERG channel, may have a risk of producing a side effect on the cardiovascular system. Therefore, the compound having the above action is expected to exhibit excellent drug efficiency and possess high safety.

The compound (I) of the present invention, a pharmaceutically acceptable salt or a hydrate thereof can be synthesized by various organic synthesis processes known to those skilled in the art. Examples thereof include the production methods described below; however, the present invention is not limited to these. Furthermore, in the following reaction schemes, R, X, Y, Z, W, $A^1$, $A^2$, $A^3$ and Cy are the same as defined above.

The "inert solvent" represents, for example, aromatic solvents such as benzene, toluene, xylene and pyridine; hydrocarbon solvents such as hexane, pentane and cyclohexane; halogenated hydrocarbon solvents such as dichloromethane, chloroform, 1,2-dichloroethane and carbon tetrachloride; ether solvents such as tetrahydrofuran, diethyl ether, 1,2-dimethoxyethane and 1,4-dioxane; ester solvents such as ethyl acetate and ethyl formate; alcohol solvents such as methanol, ethanol, isopropyl alcohol, tert-butyl alcohol and ethylene glycol; ketone solvents such as acetone and methyl ethyl ketone; amide solvents such as N,N-dimethylformamide, N-methylpyrrolidone and N,N-dimethylacetamide; sulfoxide solvents such as dimethylsulfoxide; nitrile solvents such as acetonitrile and propionitrile; water; and homogenous and non-homogeneous mixture of these solvents. These inert solvents are appropriately selected depending upon various reaction conditions known to those skilled in the art.

The "base" represents, for example, hydrides of an alkali metal or an alkaline-earth metal such as lithium hydride, sodium hydride, potassium hydride and calcium hydride; amides of an alkali metal or an alkaline-earth metal such as lithium amide, sodium amide, lithium diisopropyl amide, lithium dicyclohexyl amide, lithium hexamethyldisilazide, sodium hexamethyldisilazide and potassium hexamethyldisilazide; lower alkoxides of an alkali metal or an alkaline-earth metal such as sodium methoxide, sodium ethoxide and potassium tert-butoxide; alkyl lithiums such as butyllithium, sec-butyllithium, tert-butyllithium and methyl lithium; hydroxides of an alkali metal or an alkaline-earth metal such as sodium hydroxide, potassium hydroxide, lithium hydroxide and barium hydroxide; carbonates of an alkali metal or an alkaline-earth metal such as sodium carbonate, potassium carbonate and cesium carbonate; hydrogen carbonates of an alkali metal or an alkaline-earth metal such as sodium hydrogen carbonate and potassium hydrogen carbonate; amines such as triethylamine, N-methylmorpholine, N,N-diisopropylethylamine, 1,8-diazabicyclo[5.4.0]undec-7-ene (DBU), 1,5-diazabicyclo[4.3.0]non-5-ene (DBN) and N,N-dimethyl aniline; and basic heterocyclic compounds such as pyridine, imidazole and 2,6-lutidine. These bases are appropriately selected depending upon various reaction conditions known to those skilled in the art.

The "acid" represents, for example, an inorganic acid such as hydrochloric acid, hydrobromic acid, sulfuric acid, nitric acid and phosphoric acid, and an organic acid such as p-toluene sulfonic acid, methane sulfonic acid, trifluoroacetic acid, formic acid and acetic acid. These acids are appropriately selected depending upon various reaction conditions known to those skilled in the art.

[Production Method 1]

The compound (I) of the present invention can be produced by the method shown in Scheme 1.

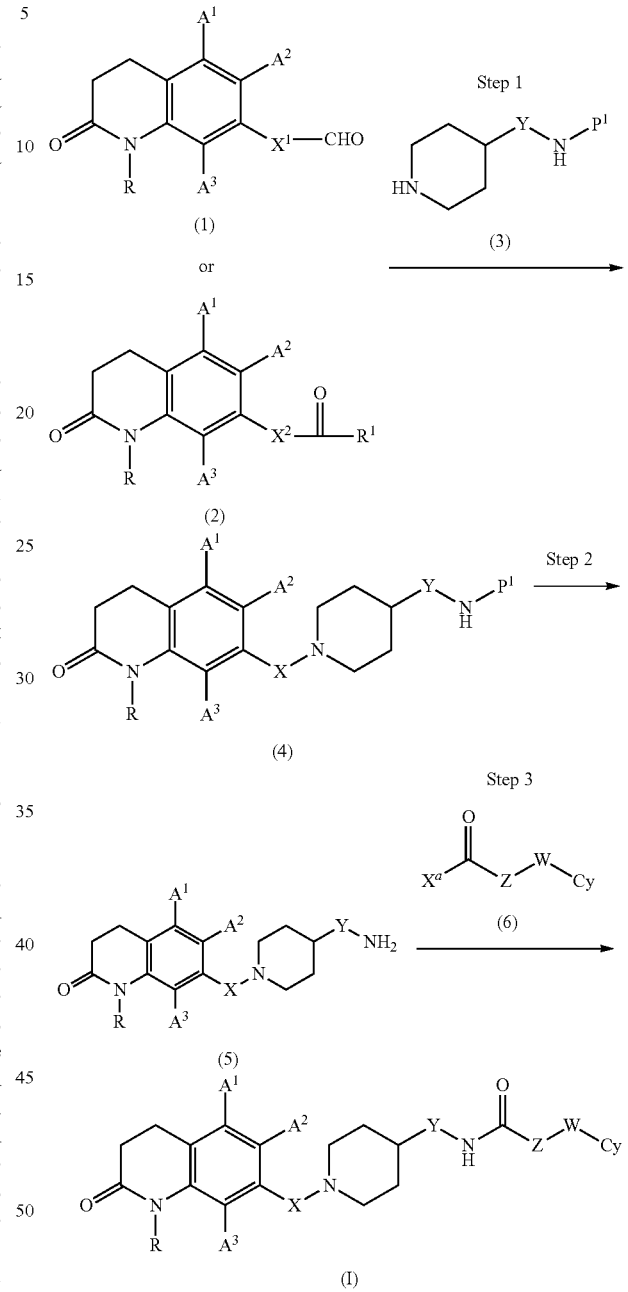

(Scheme 1)

[Formula 4]

where
  $X^1$ represents a bond or a $C_{1-5}$ alkylene group;
  $X^2$ represents a bond or a $C_{1-4}$ alkylene group;
  $X^a$ represents a halogen atom or a hydroxyl group;
  $R^1$ represents a $C_{1-5}$ alkyl group;
  with the proviso that, the sum of carbon atoms of $X^2$ and $R^1$ is 1 to 5; and
  $P^1$ represents a hydrogen atom or a protecting group of an amino group, such as a methoxycarbonyl group, an ethoxycarbonyl group, a tert-butoxycarbonyl group, a benzyloxycarbonyl group, an acetyl group or a benzyl group (see Protective Groups in Organic Synthesis, the third edition, John Wiley & Sons, INC.).

Step 1: A carbonyl compound (1) or (2) and an amine compound (3) are subjected to a reductive amination reaction using a reducing agent in an inert solvent and in the presence or absence of an acid. As a result, a compound (4) can be obtained. (see Comprehensive Organic Transformations, 1989, VCH Publishers, INC.). The carbonyl compound (1) or (2) used herein is available as a commercially available compound or a known compound. Furthermore, the carbonyl compound (1) or (2) can be synthesized by use of various organic synthesis processes known to those skilled in the art from commercially available compounds or known compounds. The reducing agent used herein is, for example, sodium triacetoxyborohydride, sodium cyanoborohydride and sodium borohydride.

Step 2: The protecting group $P^1$ of the amino group of the compound (4) is removed by use of various organic synthesis processes known to those skilled in the art (see Protective Groups in Organic Synthesis, the third edition, John Wiley & Sons, INC.). As a result, an amine compound (5) can be obtained. Furthermore, also in the case of a compound (3) where $P^1$ is a hydrogen atom, an amine compound (5) can be obtained directly by carrying out the same reductive amination reaction as in Step 1.

Step 3: The amine compound (5) and an acid halide compound (6) where $X^a$ is a halogen atom or a carboxylic acid compound (6) where $X^a$ is a hydroxyl group are subjected to an amidation reaction in an inert solvent, and in the presence or absence of a base. As a result, the compound of the presence invention (I) can be obtained. The acid halide compound (6) or the carboxylic acid compound (6) is available as a commercially available compound or a known compound. Furthermore, the acid halide compound (6) or the carboxylic acid compound (6) can be synthesized by use of various organic synthesis processes known to those skilled in the art from commercially available compounds or known compounds. The amidation reaction used herein refers to an amidation reaction using a condensing agent such as N,N'-dicyclohexylcarbodiimide, 1-ethyl-3-(3-dimethylaminopropyl)carbodiimide hydrochloride, diphenylphosphoryl azide or carbonyl diimidazole, in an inert solvent and in the presence or absence of a base, or an amidation reaction via a mixed acid anhydride using ethyl chlorocarbonate, isobutyl chlorocarbonate, pivaloyl chloride, or the like (see Fundamental and Experiment of Peptide Synthesis, 1985, Maruzen Co., Ltd.). In the amidation reaction using a condensing agent herein, if necessary, an additive such as 1-hydroxybenzotriazole can be used.

Furthermore, a carbonyl compound, which is a starting material in Scheme 1, can be produced as a compound (II) or (13) by the method shown in Scheme 2.

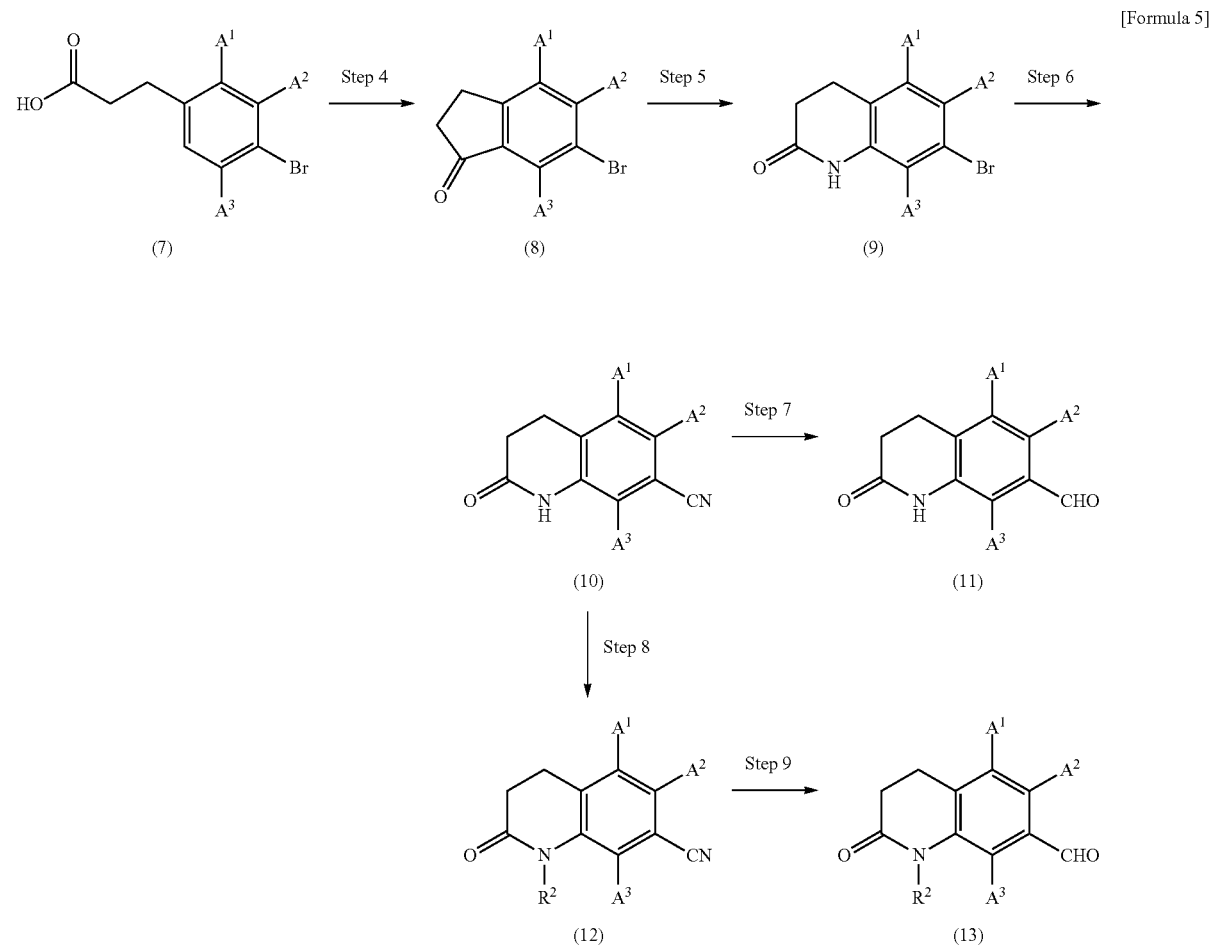

where $R^2$ represents a $C_{1-6}$ alkyl group.

Step 4: A carboxylic acid compound (7) is subjected to the Friedel-Crafts reaction in the presence of an acid catalyst. As a result, a carbonyl compound (8) can be obtained. The acid catalyst used herein refers to aluminum trichloride, chlorosulfuric acid and polyphosphoric acid (see Tetrahedron, 2007, Vol. 63, p. 389-395).

Step 5: A carbonyl compound (8) is subjected to the Schmidt reaction (see Strategic Applications of Named Reactions in Organic Synthesis, 2005, Elsevier, INC., or U.S. Patent No. 2006/0063799) using sodium azide or the like in the presence of an acid catalyst such as methane sulfonic acid, sulfuric acid, polyphosphoric acid and titanium tetrachloride. As a result, an amide compound (9) can be obtained.

Step 6: The compound (9) is reacted with zinc cyanide, copper cyanide, potassium cyanide, or the like in the presence or absence of a palladium catalyst. As a result, a nitrile compound (10) can be obtained (see, Tetrahedron, 2006, vol. 62, p. 4705-4708).

Step 7: The nitrile compound (10) is reduced in an inert solvent and in the presence of a metal catalyst. As a result, a carbonyl compound (II) can be obtained (see Comprehensive Organic Transformations, 1989, VCH Publishers, INC., or International Publication WO1996/20180). As the metal catalyst, Raney nickel and tin dichloride etc. are used.

Step 8: The nitrile compound (10) can be converted into a nitrile compound (12) by various alkylation reactions known to those skilled in the art (see Comprehensive Organic Transformations, 1989, VCH Publishers, INC.).

Step 9: The nitrile compound (12) can be converted into a carbonyl compound (13) in the same manner as in Step 7.

Furthermore, the carbonyl compound (I), which is a starting material in Scheme 1, can be produced as a carbonyl compound (17) by the method shown in Scheme 3.

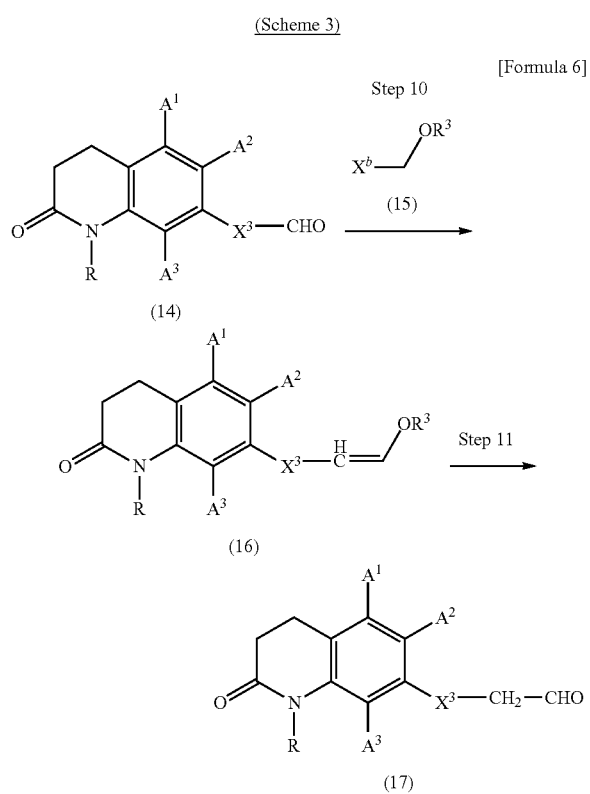

where $X^3$ represents a bond or a $C_{1-4}$ alkylene;

$X^b$ represents a group used in the Wittig reagent or the Horner-Emmons reagent (such as a phosphonium salt or a phosphorous acid diester etc.); and $R^3$ represents a $C_{1-6}$ alkyl group.

Step 10: The carbonyl compound (14) is reacted with the Wittig reagent or the Horner-Emmons reagent (15) in an inert solvent and in the presence of a base (see Comprehensive Organic Transformations, 1989, VCH Publishers, INC.). As a result, an olefin compound (16) can be obtained.

Step 11: The olefin compound (16) can be converted into a carbonyl compound (17) by various hydrolysis reactions known to those skilled in the art (see Protective Groups in Organic Synthesis, the third edition, John Wiley & Sons, INC.).

Furthermore, a carbonyl compound (I), which is a starting material in Scheme 1, can be produced as a carbonyl compound (19) by the method shown in Scheme 4.

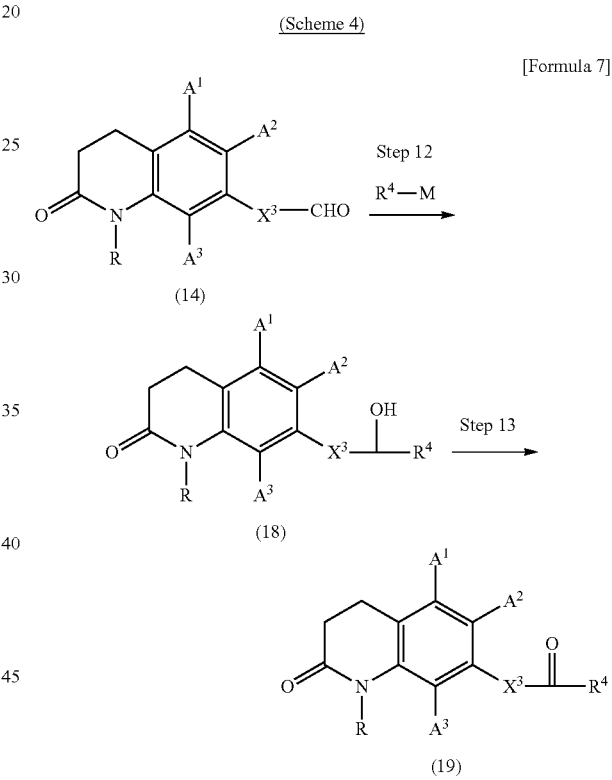

where $X^3$ is the same as defined above;

$R^4$ represents a $C_{1-5}$ alkyl group;

with the proviso that, the sum of carbon atoms of $X^3$ and $R^4$ is 1 to 5; and M represents a metal to be used in an alkylation reaction. The metal used herein represents, for example, a metal such as lithium and magnesium halide etc.

Step 12: The carbonyl compound (14) is subjected to an alkylation reaction using an organic metal reagent represented by formula $R^4$-M (see Comprehensive Organic Transformations, 1989, VCH Publishers, INC.) in an inert solvent. As a result, an alcohol compound (18) can be obtained.

Step 13: The alcohol compound (18) can be converted into a carbonyl compound (19) by an oxidation reaction known to those skilled in the art (see Oxidations in Organic Chemistry, 1990, American Chemical Society) in an inert solvent. The oxidation reaction known to those skilled in the art refers to, for example, a chromic acid oxidation reaction using pyridinium dichromate or pyridinium chlorochromate etc., a manganese oxidation reaction using manganese dioxide etc., a dimethylsulfoxide oxidation reaction using oxalyl chloride (Swern oxidation) or dicyclohexyl carbodiimide (Moffatt oxidation) etc. as an activation agent, a 2,2,6,6-tetramethyl-1-piperidinyloxy oxidation reaction (TEMPO oxidation) using a cooxidant such as sodium hypochlorite or an oxidation reaction using the Dess-Martin reagent.

Furthermore, a compound (24), which is a carbonyl compound (I) serving as a starting material in Scheme 1, where at least one of $A^1$, $A^2$ and $A^3$ is a halogen atom, can be produced by the method shown in Scheme 5.

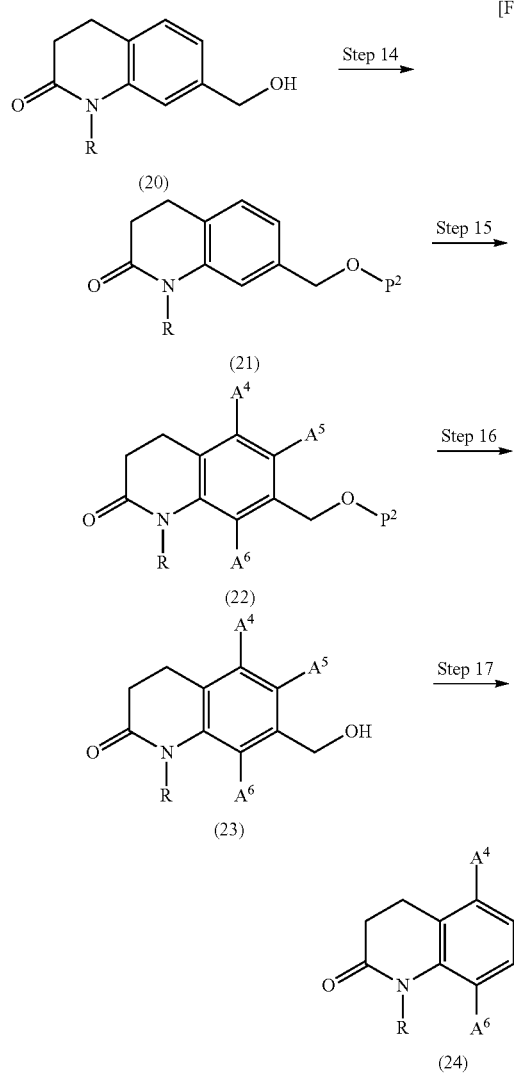

where $A^4$, $A^5$ and $A^6$, which may be the same or different, each represent a hydrogen atom or a halogen atom;

with the proviso that at least one of $A^4$, $A^5$ and $A^6$ represents a halogen atom;

$P^2$ represents a protecting group of a hydroxyl group such as a tert-butyldimethylsilyl group, a tert-butyldiphenylsilyl group, a tetrahydropyranyl group, a methoxymethyl group, an acetyl group, a benzoyl group or a benzyl group (see Protective Groups in Organic Synthesis, the third edition, John Wiley & Sons, INC.).

Step 14: The hydroxyl group of an alcohol compound (20) is protected with a protecting group such as a tert-butyldimethylsilyl group, a tert-butyldiphenylsilyl group, a tetrahydropyranyl group, a methoxymethyl group, an acetyl group, a benzoyl group or a benzyl group (see Protective Groups in Organic Synthesis, the third edition, John Wiley & Sons, INC.). As a result, a compound (21) can be obtained.

Step 15: The compound (21) is converted into a compound (22) having a halogen substituent onto an aromatic ring by various halogenation reactions known to those skilled in the art (see Comprehensive Organic Transformations, 1989, VCH Publishers, INC. or Tetrahedron Letters 1999, vol. 40, p. 2673-2676).

Step 16: The protecting group $P^2$ of the compound (22) is removed by use of various organic synthesis processes known to those skilled in the art (see Protective Groups in Organic Synthesis, the third edition, John Wiley & Sons, INC.). As a result, an alcohol compound (23) can be obtained.

Step 17: The alcohol compound (23) can be converted into the carbonyl compound (24) in the same method as in Step 13.

[Production Method 2]

The compound (I) of the present invention can be produced by the method shown in Scheme 6.

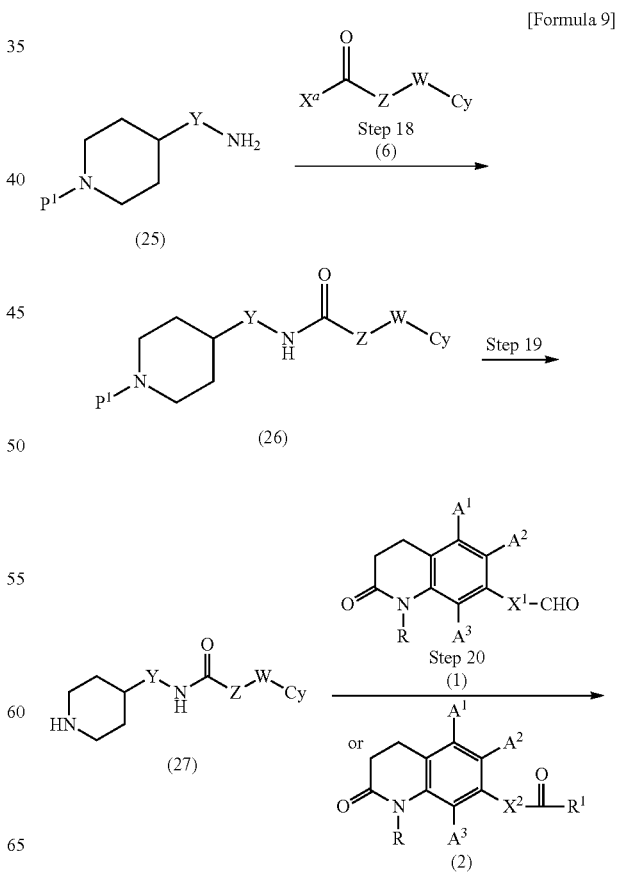

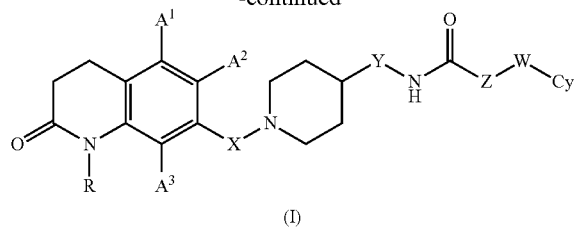

(I)

where $X^1$, $X^2$, $X^a$, $R^1$ and $P^1$ are the same as defined above.

Step 18: A compound (25) can be converted into a compound (26) in the same process as in Step 3 of Scheme 1.

Step 19: The compound (26) can be converted into a compound (27) in the same process as in Step 2 of Scheme 1. Furthermore, also in the case of a compound (25) where $P^1$ is a hydrogen atom, the same amidation reaction as in Step 3 of Scheme 1 is performed. As a result, the compound (27) can be directly obtained.

Step 20: The carbonyl compound (1) or (2) is subjected to the reductive amination reaction with the amine compound (27) in the same process as in Step 1 of Scheme 1. As a result, the compound (I) of the present invention can be obtained.

Furthermore, the nitrile compound (10) in Scheme 2 can be produced from a phenol compound (28) by the method shown in Scheme 7.

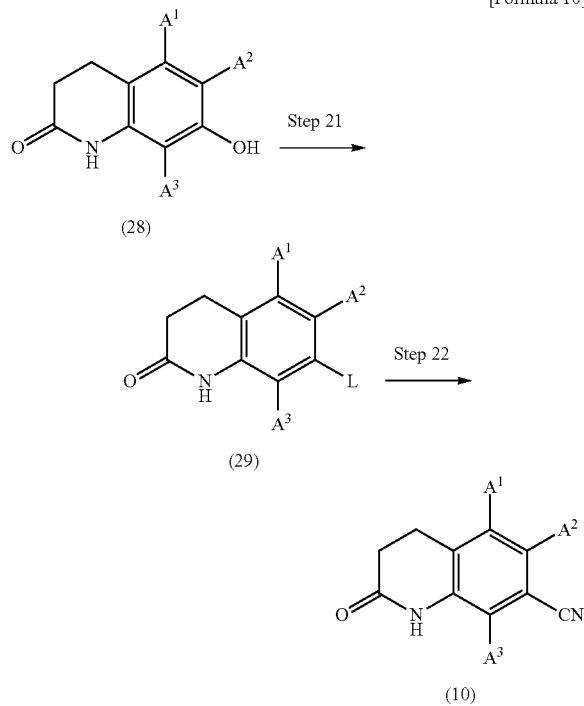

where L represents a leaving group such as a halogen atom, a methanesulfonyloxy group, a trifluoromethanesulfonyloxy group or a p-toluenesulfonyloxy group etc.

Step 21: The phenol compound (28) used herein is available as a commercially available compound or a known compound. Furthermore, the phenol compound (28) can be synthesized by use of various organic synthesis processes known to those skilled in the art from commercially available compounds or known compounds. When L represents a halogen atom, a compound (29) can be obtained by performing halogenation reaction of the hydroxyl group of the compound (28) with a halogenating agent such as bromine or oxalyl chloride in an inert solvent in the presence of trimethylphosphine, tributylphosphine, triphenylphosphine or the like, or by performing halogenation reaction of the hydroxyl group with a halogenating agent such as thionyl chloride, phosphorus trichloride, phosphorus pentachloride, phosphorus tribromide, phosphorus pentabromide or phosphorus oxychloride in an inert solvent or without a solvent in the presence or absence of a base. Alternatively, when L represents a methanesulfonyloxy group, a trifluoromethanesulfonyloxy group or a p-toluenesulfonyloxy group, the compound (29) can be obtained by reacting the hydroxyl group of the compound (28) with methanesulfonyl chloride, methanesulfonic anhydride, trifluoromethanesulfonic anhydride, N-phenyl-bis(trifluoromethanesulfonimide) or p-toluenesulfonyl chloride, for example, in an inert solvent in the presence or absence of a base. [see Comprehensive Organic Transformations, 1989, VCH Publishers, Inc.].

Step 22: The compound (29) can be converted into the nitrile compound (10) in the same process as in Step 6 of Scheme 2.

When the compound (I) of the present invention forms a salt and used as a medical drug, the salt is preferably a pharmaceutically acceptable salt. As the pharmaceutically acceptable salt, for example, a salt with an inorganic acid such as a hydrochloride, a sulfate, a hydrobromate, a nitrate or a phosphate; or a salt with an organic acid such as an acetate, an oxalate, a lactate, a citrate, a malate, a tartrate, a maleate, a fumarate, a succinate, a methanesulfonic acid, an ethanesulfonate, a benzene sulfonate or a p-toluene sulfonate may be used; however, the pharmaceutically acceptable salt is not limited to these.

Furthermore, as the pharmaceutically acceptable salt, an alkaline metal salt (for example, a sodium salt, a potassium salt), an alkaline-earth metal salt (for example, a calcium salt, a magnesium salt, a barium salt), a salt with an inorganic base such as an aluminium salt or an ammonium salt, or a salt with an organic base such as trimethylamine, triethylamine, pyridine, picoline, ethanolamine, diethanolamine, triethanolamine, dicyclohexylamine or N,N-dibenzylethylenediamine may be mentioned.

When the compound (I) of the present invention includes an optical isomer, a stereoisomer, a regioisomer and a rotational isomer, a single compound and a mixture thereof are included in the compound of the present invention. Furthermore, when the compound (I) of the present invention forms a hydrate or a solvate, these are also included in the range of the present invention. Furthermore, the compound (I) of the present invention may be labeled with an isotope (for example, D, $^3$H, $^{13}$C, $^{14}$C, $^{15}$N, $^{35}$S, $^{125}$I etc.).

The MCH receptor antagonist and medical drug of the present invention are each produced of the compound (I) of the present invention, a pharmaceutically acceptable salt or a hydrate singly or together with a pharmacologically acceptable carrier into a preparation by a well-known method. As the pharmacologically acceptable carrier, various types of organic or inorganic carrier substances customarily used as materials for preparations may be mentioned. For example, mention may be made of an excipient to be used in solid preparations (for example, lactose, white sugar, D-mannitol, starch, cornstarch, crystalline cellulose, light silicic acid anhydride), a lubricant (for example, magnesium stearate, calcium strearate, talc, colloidal silica), a binder (for example, crystalline cellulose, white sugar, D-mannitol, dextrin, hydroxypropylcellulose, hydroxypropylmethylcellulose, polyvinylpyrrolidone, starch, sucrose, gelatin, methylcellulose, sodium carboxymethylcellulose), a disintegrator (for example, sucrose, carboxymethylcellulose, calcium carboxymethylcellulose, sodium croscarmellose, sodium carboxymethyl starch, hydroxypropylcellulose with a low degree of substitution), or a solvent to be used in liquid preparations (for example, injection water, alcohol, propylene glycol, macrogol, sesame oil, corn oil), a solubilization agent (for example, polyethylene glycol, propylene glycol, D-mannitol, benzyl benzoate, ethanol, trisaminomethane, cholesterol, triethnaolamine, sodium carbonate, sodium citrate), a suspension agent (for example, a surfactant such as stearyl triethanol amine, sodium lauryl sulfate, lauryl amino propionate, lecithin, benzalkonium chloride, benzethonium chloride and glycerin monostearate, or a hydrophilic polymer such as polyvinyl alcohol, polyvinyl pyrrolidone, sodium carboxymethylcellulose, methylcellulose, hydroxymethylcellulose and hydroxypropylcellulose), an isotonic agent (for example, glucose, D-sorbitol, sodium chloride, glycerin, D-mannitol), a buffer (for example, a phosphate, an acetate, a carbonate, a citrate) or a soothing agent (for example, benzyl alcohol) etc. Furthermore, in producing a preparation, if necessary, an antiseptic agent (for example, paraoxybenzoates, chloro butanol, benzyl alcohol, phenethyl alcohol, dehydroacetic acid, sorbic acid), an antioxidant (for example, sulfite, ascorbic acid), a colorant, a sweetener, an adsorbent and a moisturizer etc. can be used.

The MCH receptor antagonist and medical drug of the present invention can be administered orally or parenterally (for example, intravenous, local, rectal injection). Examples of the dosage form include tablets (including sugar-coating tablets and film-coating tablets), powders, granules, dust formulations, troches, capsules (including soft capsules), liquids, injections (for example, a subcutaneous injection, an intravenous injection, an intramuscular injection, an intraperitoneal injection), external preparations (for example, a transnasal administration agent, a transdermal preparation, an ointment, a cream), suppositories (for example, a rectal suppository, a vagina suppository), sustained release agents (for example, sustained release microcapsule), pellets and drops. All can be produced by a customary preparation technique (for example, the methods described in the 15th revised Japanese Pharmacopoeia).

The dose of the MCH receptor antagonist and medical drug of the present invention is appropriately selected depending upon the administration target, administration route, disease, age of a patient, body weight and symptom. For example, when an adult patient is treated, the dose is 1 to 2000 mg per day. The dose is administered at a time or separately in parts per day.

When the MCH receptor antagonist is used as an active ingredient of a medical drug, it should be noted that it is intended to be applied not only to humans but also to other mammalians. For example, according to recent progress in the field of animal healthcare, it is considered that the MCH receptor antagonist may be used for treating obesity of domestic animals (for example, cats, dogs) and also used for other domestic animals (for example, edible animals such as cow, fowl, fish) whose disease or disorder is not known.

EXAMPLES

The present invention will be more specifically described by way of the following examples; however, these examples should not be construed as limiting the invention and may be modified within the scope of the invention.

The "room temperature" referred to in the examples, represents 0° C. to 40° C. "Silica gel 60 N" and "Chromatorex NH" used in purification by use of column chromatography were commercially available from Kanto Chemical Co., Inc. and Fuji Silysia, respectively.

In the examples, the data that were measured by equipment were measured by the following measuring equipment.

MS spectrum: Shimadzu LCMS-2010EV or micromass Platform LC

NMR spectrum: 600 MHz (JNM-ECA 600, JEOL Ltd.) or 200 MHz (GEMINI 2000/200, Varian Inc.)

The compounds in the examples were designated in accordance with ACD/Name (ACD/Labs 11.00, Advanced Chemistry Development Inc.).

The abbreviations used in the examples are shown below:
$Ac_2O$ (acetic anhydride), AcOH (acetic acid), APCI (atmospheric pressure chemical ionization), brs (broad singlet), $CDCl_3$ (deuterated chloroform), $CHCl_3$ (chloroform), $CH_3CN$ (acetonitrile), d (doublet), dd (double doublet), ddd (double double doublet), DMAP (N,N-dimethyl-4-aminopyridine), DMF (N,N-dimethylformamide), DMSO-$d_6$ (deuterated dimethylsulfoxide), dt (double triplet), EDC [1-ethyl-3-(3-dimethylaminopropyl)carbodiimide], EI (electronic ionization), ESI (electrospray ionization), $Et_3N$ (triethylamine), $Et_2O$ (diethylether), EtOAc (ethyl acetate), EtOH (ethanol), H (proton), HCl (hydrochloride or hydrochloric acid), $H_2O$ (water), HOBt (1-hydroxybenzotriazol), Hz (hertz), IPA (isopropyl alcohol), IPE (isopropyl ether), J (coupling constant), $K_2CO_3$ (potassium carbonate), m (multiplet), MeI (methyl iodide), MeMgBr (methylmagnesium bromide), MeOH (methanol), MeOH-$d_4$ (deuterated methanol), $MgSO_4$ (magnesium sulfate), $MnO_2$ (manganese dioxide), MS (mass spectrometry), $NaBH_4$ (sodium borohydride), NaH (sodium hydride), $NaHCO_3$ (sodium hydrogen carbonate), $Na_2SO_4$ (sodium sulfate), $NH_4Cl$ (ammonium chloride), NMR (nuclear magnetic resonance spectroscopy), $NaBH(OAc)_3$ (sodium triacetoxyborohydride), $NaNH_2$ (sodium amide), NaOH (sodium hydroxide), $Pd_2(dba)_3$ [tris(dibenzylideneacetone)dipalladium], $Ph_2PCH_2OMe.Br$ [(methoxymethyl)triphenylphosphonium bromide], $iPr_2Net$ (diisopropylethylamine), q (quartet), s (singlet), t (triplet), td (triple doublet), THF (tetrahydrofuran), TMEDA (tetramethylethylenediamine), v/v (volume/volume), Xantphos [4,5-bis(diphenylphosphino)-9,9-dimethyl xanthene].

Example 1

Synthesis of 3-methoxy-N-{1-[(2-oxo-1,2,3,4-tetrahydroquinolin-7-yl)methyl]piperidin-4-yl}benzamide Step 1-1: To chlorosulfuric acid (1.19 L) was added 3-(4-bromophenyl)propanoic acid (91.1 g) under ice cooling and the mixture was stirred for 2 hours. To $H_2O$ (2.00 L), the reaction mixture was slowly added under ice cooling, and extracted 6 times with $CHCl_3$. The combined organic layers were washed with a saturated aqueous $NaHCO_3$ solution, dried over $Na_2SO_4$ and concentrated under reduced pressure. To the resultant residue, MeOH was added and the mixture was heated to reflux for 30 minutes. A solid substance was obtained by filtration to give solid A. The filtrate was concentrated under reduced pressure and solid B was obtained in the same manner. Thereafter, the filtrate was again concentrated under reduced pressure and solid C was obtained in the same manner. Solids A, B and C were combined to obtain 6-bromo-2,3-dihydro-1H-inden-1-one (59.3 g, a light yellow solid).

$^1$H NMR (600 MHz, CDCl$_3$, δ): 2.66-2.75 (m, 2H), 3.04-3.12 (m, 2H), 7.36 (d, J=8.3 Hz, 1H), 7.67 (dd, J=8.0, 2.1 Hz, 1H), 7.86 (d, J=1.8 Hz, 1H); ESI/APCI MS m/z 210 [M+H]$^+$.

Step 1-2: To the CHCl$_3$ solution (560 mL) of the compound (39.5 g) obtained in Step 1-1 and methanesulfonic acid (122 mL), sodium azide (36.5 g) was added separately in parts under ice cooling, and then the mixture was heated to reflux for 2.5 hours. To H$_2$O (400 mL), the reaction mixture was added under ice cooling, adjusted to pH 9 with 28% ammonia water and extracted with CHCl$_3$ three times. The combined organic layers were dried over Na$_2$SO$_4$ and concentrated under reduced pressure. Thereafter, the residue was purified by column chromatography (silica gel 60 N, mobile phase: EtOAc/hexane=50/50 to 75/25; v/v). The solid substance obtained was suspended in a solution of EtOAc/hexane (1/1; v/v) and the mixture was stirred at room temperature for one hour. A solid substance was obtained by filtration to give 7-bromo-3,4-dihydroquinolin-2(1H)-one (15.5 g, a light yellow solid).

$^1$H NMR (200 MHz, CDCl$_3$, δ): 2.59-2.68 (m, 2H), 2.88-2.97 (m, 2H), 6.91-7.16 (m, 3H), 8.27 (brs, 1H); ESI/APCI MS m/z 226 [M+H]$^+$.

Step 1-3: To a DMF solution (14.5 mL) of the compound (3.00 g) obtained in Step 1-2, zinc cyanide (1.04 g), Pd$_2$(dba)$_3$ (122 mg), Xantphos (154 mg) and TMEDA (590 μL) were added and the mixture was stirred under microwave irradiation (180° C.) for 5 minutes. To the reaction mixture, CHCl$_3$ was added and the mixture was filtrated by Celite and washed with DMF. The filtrate was concentrated under reduced pressure. The residue was purified by column chromatography (silica gel 60 N, mobile phase: EtOAc/hexane=50/50 to 100/0; v/v). To the solid substance obtained, EtOAc was added at room temperature and the mixture was stirred for 30 minutes. A solid substance was obtained by filtration and washed with EtOAc to obtain 2-oxo-1,2,3,4-tetrahydroquinoline-7-carbonitrile (15.5 g, a light yellow solid).

$^1$H NMR (600 MHz, CDCl$_3$, δ): 2.64-2.68 (m, 2H), 3.00-3.04 (m, 2H), 7.04 (s, 1H), 7.23-7.29 (m, 2H), 8.46 (brs, 1H); ESI/APCI MS m/z 173 [M+H]$^+$.

Step 1-4: To a formic acid (250 mL) solution of the compound (32.6 g) obtained in Step 1-3, Raney nickel catalyst (50.0 g) was added and the mixture was stirred at 50° C. for 2 hours. After the reaction mixture was filtrated by Celite, the filtrate was concentrated under reduced pressure. To the residue, a saturated aqueous NaHCO$_3$ solution was added and the mixture was adjusted to pH 6 and filtrated to obtain solid A. The filtrate was extracted three times with CHCl$_3$ and the combined organic layers were dried over Na$_2$SO$_4$ and concentrated under reduced pressure. The residue and solid A were combined and suspended in a solution mixture of EtOAc/CHCl$_3$/acetone (10/10/1; v/v/v) and the mixture was stirred at room temperature for one hour and filtrated to obtain 2-oxo-1,2,3,4-tetrahydroquinoline-7-carbaldehyde (19.8 g, a light yellow solid).

$^1$H NMR (200 MHz, CDCl$_3$, δ): 2.65-2.76 (m, 2H), 3.02-3.13 (m, 2H), 7.31-7.38 (m, 2H), 7.49-7.55 (m, 1H), 9.13 (brs, 1H), 9.95 (s, 1H); ESI/APCI MS m/z 176 [M+H]$^+$.

Step 1-5: A solution of the compound (19.8 g) obtained in Step 1-4 and tert-butyl piperidin-4-ylcarbamate (24.8 g) in CHCl$_3$ (450 mL) was stirred at 70° C. for 1.5 hours and allowed to cool to room temperature. Thereafter, NaBH(OAc)$_3$ (35.9 g) was added to the mixture under ice cooling and the mixture was stirred at room temperature for 12 hours. A saturated aqueous NaHCO$_3$ solution was added to the reaction mixture and then a water layer and an organic layer were separated. The water layer was extracted three times with CHCl$_3$. The combined organic layers were dried over Na$_2$SO$_4$ and concentrated under reduced pressure. The residue was purified by column chromatography (silica gel 60 N, mobile phase: MeOH/CHCl$_3$=33/66 to 100/0; v/v) to obtain tert-butyl {1-[(2-oxo-1,2,3,4-tetrahydroquinolin-7-yl)methyl]piperidin-4-yl}carbamate (37.8 g, a colorless solid).

$^1$H NMR (600 MHz, CDCl$_3$, δ): 1.35-1.51 (m, 11H), 1.82-1.96 (m, 2H), 2.07 (t, J=10.5 Hz, 2H), 2.49-2.66 (m, 2H), 2.78 (brs, 2H), 2.93 (t, J=7.6 Hz, 2H), 3.29-3.55 (m, 3H), 4.48 (brs, 1H), 6.76 (s, 1H), 6.90 (d, J=7.3 Hz, 1H), 7.08 (d, J=7.8 Hz, 1H), 8.37 (brs, 1H); ESI/APCI MS m/z 360 [M+H]$^+$.

Step 1-6: To an EtOAc (130 mL) solution of the compound (37.8 g) obtained in Step 1-5, 4 M HCl/EtOAc solution (263 mL) was added under ice cooling and the mixture was stirred at room temperature for one hour. The reaction mixture was concentrated under reduced pressure. The residue was suspended in EtOAc (200 mL) and filtrated to obtain a solid. To the solid, CHCl$_3$ (200 mL) and H$_2$O (200 mL) were added and the mixture was stirred for 15 minutes. After a water layer and an organic layer were separated, the water layer was washed with CHCl$_3$ twice. To the water layer, a 2 M aqueous NaOH solution was added to adjust to pH 10 and thereafter the solution was extracted 30 times with CHCl$_3$. The combined organic layers were dried over Na$_2$SO$_4$ and concentrated under reduced pressure. The residue was purified by column chromatography (Chromatorex NH, mobile phase: MeOH/CHCl$_3$=1/4; v/v) to obtain 7-[(4-aminopiperidin-1-yl)methyl]-3,4-dihydroquinolin-2(1H)-one (17.9 g, a colorless solid).

$^1$H NMR (600 MHz, CDCl$_3$, δ): 1.32-1.49 (m, 2H), 1.74-1.88 (m, 2H), 1.93-2.09 (m, 2H), 2.54-2.70 (m, 3H), 2.80 (d, J=11.9 Hz, 2H), 2.93 (t, J=7.6 Hz, 2H), 3.41 (s, 2H), 6.74 (s, 1H), 6.90 (d, J=9.2 Hz, 1H), 7.07 (d, J=7.3 Hz, 1H), 8.28 (brs, 1H); ESI/APCI MS m/z 260 [M+H]$^+$.

Step 1-7: To a CHCl$_3$ (5.00 mL) solution of the compound (250 mg) obtained in Step 1-6, iPr$_2$NEt (370 μL) and 3-methoxybenzoyl chloride (180 mg) were added and the mixture was stirred at room temperature for three days. To the reaction mixture, a saturated aqueous NaHCO$_3$ solution was added and the solution was extracted with CHCl$_3$ four times. The combined organic layers were dried over Na$_2$SO$_4$ and concentrated under reduced pressure. The residue was purified by column chromatography [(silica gel 60 N, mobile phase: MeOH/CHCl$_3$=0/100 to 10/90; v/v) and (Chromatorex NH, mobile phase: CHCl$_3$) in this order] to obtain a solid. To the solid obtained, IPA was added at room temperature and the mixture was stirred for one hour, filtrated and washed with IPA and hexane to obtain the titled compound (159 mg, a colorless solid).

$^1$H NMR (600 MHz, CDCl$_3$, δ): 1.48-1.62 (m, 2H), 1.94-2.06 (m, 2H), 2.10-2.21 (m, 2H), 2.57-2.67 (m, 2H), 2.78-2.87 (m, 2H), 2.90-2.99 (m, 2H), 3.44 (s, 2H), 3.85 (s, 3H), 3.94-4.05 (m, 1H), 6.01 (d, J=7.8 Hz, 1H), 6.74 (s, 1H), 6.91 (d, J=7.3 Hz, 1H), 7.02 (dd, J=7.6, 2.1 Hz, 1H), 7.09 (d, J=7.8 Hz, 1H), 7.21-7.27 (m, 1H), 7.29-7.35 (m, 2H), 7.85 (s, 1H); ESI/APCI MS m/z 394 [M+H]$^+$.

Example 2

Synthesis of 3-methoxy-N-{1-[(2-oxo-1,2,3,4-tetrahydroquinolin-7-yl)methyl]piperidin-4-yl}benzamide monohydrochloride, monohydrate To an EtOAc (1.70 mL) suspension of the compound (167 mg) obtained in Step 1-7, a 4 M HCl/EtOAc solution (140 μL)

was added and the mixture was stirred at room temperature for 1.5 hours and filtrated to obtain the titled compound (160 mg, a colorless solid).

$^1$H NMR (600 MHz, MeOH-d$_4$, δ): 1.98 (brs, 2H), 2.18 (brs, 2H), 2.53-2.62 (m, 2H), 2.98 (t, J=7.6 Hz, 2H), 3.03-3.19 (m, 2H), 3.50 (brs, 2H), 3.81 (s, 3H), 4.11 (brs, 1H), 4.23 (brs, 2H), 6.98 (s, 1H), 7.05-7.15 (m, 2H), 7.27-7.39 (m, 4H); ESI/APCI MS m/z 394 [M(free)+H]$^+$ The compounds of Example 3 to Example 30 were obtained in the same process as in Example 1.

TABLE 1

| Example No. | Name of compound | Physical property data |
|---|---|---|
| 3 | 3-fluoro-N-{1-[(2-oxo-1,2,3,4-tetrahydroquinolin-7-yl)methyl]piperidin-4-yl}benzamide | $^1$H NMR (600 MHz, DMSO-d$_6$, δ): 1.46-1.59 (m, 2H), 1.73-1.76 (m, 2H), 1.95-2.01 (m, 2H), 2.37-2.43 (m, 2H), 2.73-2.86 (m, 4H), 3.32-3.35 (m, 2H), 3.70-3.80 (m, 1H), 6.77-6.82 (m, 2H), 7.06 (d, J = 7.3 Hz, 1H), 7.29-7.37 (m, 1H), 7.47 (td, J = 8.0, 6.0 Hz, 1H), 7.60 (dd, J = 9.6, 2.3 Hz, 1H), 7.65 (d, J = 7.8 Hz, 1H), 8.28-8.33 (m, 1H), 10.00 (s, 1H); ESI/APCI MS m/z 382 [M + H]$^+$. |
| 4 | 3,5-difluoro-N-{1-[(2-oxo-1,2,3,4-tetrahydroquinolin-7-yl)methyl]piperidin-4-yl}benzamide | $^1$H NMR (600 MHz, DMSO-d$_6$, δ): 1.45-1.57 (m, 2H), 1.73-1.76 (m, 2H), 1.95-2.00 (m, 2H), 2.37-2.42 (m, 2H), 2.74-2.83 (m, 4H), 3.33 (s, 2H), 3.65-3.76 (m, 1H), 6.76-6.83 (m, 2H), 7.06 (d, J = 7.8 Hz, 1H), 7.40-7.45 (m, 1H), 7.48-7.55 (m, 2H), 8.38 (d, J = 7.8 Hz, 1H), 10.00 (s, 1H); ESI/APCI MS m/z 400 [M + H]$^+$. |
| 5 | 3,4-difluoro-N-{1-[(2-oxo-1,2,3,4-tetrahydroquinolin-7-yl)methyl]piperidin-4-yl}benzamide | $^1$H NMR (600 MHz, DMSO-d$_6$, δ): 1.46-1.57 (m, 2H), 1.73-1.76 (m, 2H), 1.95-2.01 (m, 2H), 2.37-2.42 (m, 2H), 2.73-2.84 (m, 4H), 3.33 (s, 2H), 3.65-3.75 (m, 1H), 6.76-6.82 (m, 2H), 7.06 (d, J = 7.3 Hz, 1H), 7.46-7.56 (m, 1H), 7.70 (dd, J = 8.0, 3.9 Hz, 1H), 7.83-7.89 (m, 1H), 8.31 (d, J = 7.3 Hz, 1H), 10.00 (s, 1H); ESI/APCI MS m/z 400 [M + H]$^+$. |
| 6 | 4-fluoro-N-{1-[(2-oxo-1,2,3,4-tetrahydroquinolin-7-yl)methyl]piperidin-4-yl}benzamide | $^1$H NMR (600 MHz, CDCl$_3$, δ): 1.51-1.62 (m, 2H), 1.97-2.07 (m, 2H), 2.10-2.24 (m, 2H), 2.57-2.68 (m, 2H), 2.77-2.91 (m, 2H), 2.95 (t, J = 7.6 Hz, 2H), 3.46 (s, 2H), 3.94-4.07 (m, 1H), 6.01 (brs, 1H), 6.75 (s, 1H), 6.92 (d, J = 7.8 Hz, 1H), 7.05-7.15 (m, 3H), 7.65 (brs, 1H), 7.78 (dd, J = 8.7, 5.0 Hz, 2H); ESI/APCI MS m/z 382 [M + H]$^+$. |
| 7 | 3-chloro-N-{1-[(2-oxo-1,2,3,4-tetrahydroquinolin-7-yl)methyl]piperidin-4-yl}benzamide | $^1$H NMR (600 MHz, CDCl$_3$, δ): 1.55-1.65 (m, 2H), 1.94-2.05 (m, 2H), 2.10-2.22 (m, 2H), 2.57-2.68 (m, 2H), 2.78-2.90 (m, 2H), 2.94 (t, J = 7.6 Hz, 2H), 3.44 (s, 2H), 3.95-4.08 (m, 1H), 6.25 (d, J = 7.8 Hz, 1H), 6.77 (s, 1H), 6.90 (d, J = 6.4 Hz, 1H), 7.05-7.13 (m, 1H), 7.32-7.40 (m, 1H), 7.43-7.49 (m, 1H), 7.65 (d, J = 7.8 Hz, 1H), 7.78 (s, 1H), 7.88 (brs, 1H); ESI/APCI MS m/z 398 [M + H]$^+$. |
| 8 | 3-methyl-N-{1-[(2-oxo-1,2,3,4-tetrahydroquinolin-7-yl)methyl]piperidin-4-yl}benzamide | $^1$H NMR (600 MHz, CDCl$_3$, δ): 1.48-1.57 (m, 2H), 1.96-2.06 (m, 2H), 2.10-2.21 (m, 2H), 2.39 (s, 3H), 2.56-2.68 (m, 2H), 2.79-2.88 (m, 2H), 2.94 (t, J = 7.6 Hz, 2H), 3.45 (s, 2H), 3.94-4.07 (m, 1H), 5.94 (d, J = 7.8 Hz, 1H), 6.72 (s, 1H), 6.92 (d, J = 7.3 Hz, 1H), 7.05-7.13 (m, 1H), 7.26-7.34 (m, 2H), 7.50 (d, J = 4.1 Hz, 2H), 7.56 (s, 1H); ESI/APCI MS m/z 378 [M + H]$^+$. |
| 9 | N-{1-[(2-oxo-1,2,3,4-tetrahydroquinolin-7-yl)methyl]piperidin-4-yl}-3-(trifluoromethyl)benzamide | $^1$H NMR (600 MHz, CDCl$_3$, δ): 1.57-1.64 (m, 2H), 1.99-2.05 (m, 2H), 2.13-2.20 (m, 2H), 2.60-2.64 (m, 2H), 2.82-2.89 (m, 2H), 2.94 (t, J = 7.6 Hz, 2H), 3.45 (s, 2H), 4.00-4.07 (m, 1H), 6.25 (d, J = 7.3 Hz, 1H), 6.76 (s, 1H), 6.91 (d, J = 7.3 Hz, 1H), 7.10 (d, J = 7.3 Hz, 1H), 7.56 (t, J = 7.8 Hz, 1H), 7.74 (d, J = 7.8 Hz, 1H), 7.84 (brs, 1H), 7.96 (d, J = 7.8 Hz, 1H), 8.03 (s, 1H); ESI/APCI MS m/z 432 [M + H]$^+$. |
| 10 | 3,5-dichloro-N-{1-[(2-oxo-1,2,3,4-tetrahydroquinolin-7-yl)methyl]piperidin-4-yl}benzamide | $^1$H NMR (600 MHz, CDCl$_3$, δ): 1.61-1.68 (m, 2H), 1.92-2.03 (m, 2H), 2.11-2.17 (m, 2H), 2.63-2.66 (m, 2H), 2.85-2.91 (m, 2H), 2.94 (t, J = 7.3 Hz, 2H), 3.44 (s, 2H), 3.99-4.05 (m, 1H), 6.61 (brs, 1H), 6.80 (s, 1H), 6.88 (d, J = 8.7 Hz, 1H), 7.09 (d, J = 7.3 Hz, 1H), 7.46 (t, J = 2.1 Hz, 1H), 7.72 (d, J = 1.8 Hz, 2H), 8.21 (brs, 1H); ESI/APCI MS m/z 432 [M + H]$^+$. |
| 11 | 4-chloro-N-{1-[(2-oxo-1,2,3,4-tetrahydroquinolin-7-yl)methyl]piperidin-4-yl}benzamide | $^1$H NMR (600 MHz, CDCl$_3$, δ): 1.52-1.61 (m, 2H), 1.96-2.04 (m, 2H), 2.15-2.18 (m, 2H), 2.59-2.65 (m, 2H), 2.84-2.86 (m, 2H), 2.94 (t, J = 7.6 Hz, 2H), 3.44 (s, 2H), 3.95-4.04 (m, 1H), 6.08 (d, J = 7.8 Hz, 1H), 6.75 (s, 1H), 6.91 (d, J = 7.8 Hz, 1H), 7.09 (d, J = 7.8 Hz, 1H), 7.37-7.41 (m, 2H), 7.70 (d, J = 8.7 Hz, 2H), 7.81 (s, 1H); ESI/APCI MS m/z 398 [M + H]$^+$. |
| 12 | 3,4-dichloro-N-{1-[(2-oxo-1,2,3,4-tetrahydroquinolin-7-yl)methyl]piperidin-4-yl}benzamide | $^1$H NMR (600 MHz, CDCl$_3$, δ): 1.59-1.69 (m, 2H), 1.94-2.02 (m, 2H), 2.15-2.17 (m, 2H), 2.61-2.68 (m, 2H), 2.88-2.90 (m, 2H), 2.95 (t, J = 7.6 Hz, 2H), 3.45 (s, 2H), 3.97-4.07 (m, 1H), 6.54-6.60 (m, 1H), 6.81 (s, 1H), 6.90 (d, J = 7.3 Hz, 1H), 7.10 (d, J = 7.8 Hz, 1H), 7.50 (d, J = 8.3 Hz, 1H), 7.67 (dd, J = 8.3, 2.3 Hz, 1H), 7.96 (d, J = 1.8 Hz, 1H), 8.29 (brs, 1H); ESI/APCI MS m/z 432 [M + H]$^+$. |
| 13 | N-{1-[(2-oxo-1,2,3,4-tetrahydroquinolin-7-yl)methyl]piperidin-4-yl}-3-(trifluoromethoxy)benzamide | $^1$H NMR (600 MHz, CDCl$_3$, δ): 1.55-1.65 (m, 2H), 1.94-2.04 (m, 2H), 2.15-2.18 (m, 2H), 2.59-2.66 (m, 2H), 2.86-2.88 (m, 2H), 2.94-2.96 (m, 2H), 3.44 (s, 2H), 3.96-4.08 (m, 1H), 6.34 (d, J = 8.3 Hz, 1H), 6.78 (s, 1H), 6.90 (d, J = 7.8 Hz, 1H), 7.09 (d, J = 7.3 Hz, 1H), 7.34 (d, J = 8.3 Hz, 1H), 7.45 (t, J = 8.0 Hz, 1H), 7.66-7.72 (m, 2H), 8.11 (s, 1H); ESI/APCI MS m/z 448 [M + H]$^+$. |

TABLE 1-continued

| Example No. | Name of compound | Physical property data |
|---|---|---|
| 14 | 4-fluoro-3-methyl-N-{1-[(2-oxo-1,2,3,4-tetrahydroquinolin-7-yl)methyl]piperidin-4-yl}benzamide | $^1$H NMR (600 MHz, CDCl$_3$, δ): 1.53-1.61 (m, 2H), 1.96-2.05 (m, 2H), 2.11-2.19 (m, 2H), 2.30 (s, 3H), 2.60-2.64 (m, 2H), 2.81-2.88 (m, 2H), 2.94 (t, J = 7.6 Hz, 2H), 3.44 (s, 2H), 3.96-4.03 (m, 1H), 6.07 (d, J = 7.8 Hz, 1H), 6.76 (s, 1H), 6.90 (d, J = 7.3 Hz, 1H), 7.02 (t, J = 8.9 Hz, 1H), 7.07-7.10 (m, 1H), 7.54-7.57 (m, 1H), 7.63 (d, J = 7.3 Hz, 1H), 7.90 (s, 1H); ESI/APCI MS m/z 396 [M + H]$^+$. |
| 15 | 4-fluoro-N-{1-[(2-oxo-1,2,3,4-tetrahydroquinolin-7-yl)methyl]piperidin-4-yl}-3-(trifluoromethyl)benzamide | $^1$H NMR (600 MHz, CDCl$_3$, δ): 1.62-1.70 (m, 2H), 1.93-2.02 (m, 2H), 2.14 (t, J = 11.2 Hz, 2H), 2.54-2.64 (m, 2H), 2.84-2.96 (m, 4H), 3.44 (s, 2H), 4.01-4.08 (m, 1H), 6.79-6.89 (m, 3H), 7.09 (d, J = 7.3 Hz, 1H), 7.21-7.27 (m, 1H), 8.05-8.10 (m, 1H), 8.12-8.15 (m, 1H), 8.56 (brs, 1H); ESI/APCI MS m/z 450 [M + H]$^+$. |
| 16 | 4-methyl-N-{1-[(2-oxo-1,2,3,4-tetrahydroquinolin-7-yl)methyl]piperidin-4-yl}benzamide | $^1$H NMR (600 MHz, CDCl$_3$, δ): 1.51-1.58 (m, 2H), 1.97-2.02 (m, 2H), 2.11-2.18 (m, 2H), 2.37 (s, 3H), 2.59-2.63 (m, 2H), 2.77-2.87 (m, 2H), 2.93 (t, J = 7.3 Hz, 2H), 3.43 (s, 2H), 3.96-4.03 (m, 1H), 6.00 (d, J = 7.8 Hz, 1H), 6.73 (s, 1H), 6.89-6.91 (m, 1H), 7.07-7.09 (m, 1H), 7.21 (d, J = 7.8 Hz, 2H), 7.63 (d, J = 8.3 Hz, 2H), 7.75 (brs, 1H); ESI/APCI MS m/z 378 [M + H]$^+$. |
| 17 | 3-fluoro-4-methyl-N-{1-[(2-oxo-1,2,3,4-tetrahydroquinolin-7-yl)methyl]piperidin-4-yl}benzamide | $^1$H NMR (600 MHz, CDCl$_3$, δ): 1.51-1.64 (m, 2H), 1.94-2.03 (m, 2H), 2.07-2.19 (m, 2H), 2.29 (s, 3H), 2.55-2.67 (m, 2H), 2.80-2.86 (m, 2H), 2.89-2.98 (m, 2H), 3.43 (s, 2H), 3.95-4.04 (m, 1H), 6.21 (d, J = 7.8 Hz, 1H), 6.76 (s, 1H), 6.89 (d, J = 7.8 Hz, 1H), 7.08 (d, J = 7.3 Hz, 1H), 7.18-7.27 (m, 1H), 7.38-7.50 (m, 2H), 8.07 (s, 1H); ESI/APCI MS m/z 396 [M + H]$^+$. |
| 18 | 3-fluoro-N-{1-[(2-oxo-1,2,3,4-tetrahydroquinolin-7-yl)methyl]piperidin-4-yl}-5-(trifluoromethyl)benzamide | $^1$H NMR (600 MHz, CDCl$_3$, δ): 1.66-1.79 (m, 2H), 1.92-2.02 (m, 2H), 2.10-2.21 (m, 2H), 2.58-2.65 (m, 2H), 2.87-2.98 (m, 4H), 3.44 (s, 2H), 4.03-4.12 (m, 1H), 6.83-6.90 (m, 2H), 7.07-7.12 (m, 1H), 7.11-7.19 (m, 1H), 7.43 (d, J = 7.8 Hz, 1H), 7.86 (d, J = 9.2 Hz, 1H), 7.96 (s, 1H), 8.68 (brs, 1H); ESI/APCI MS m/z 450 [M + H]$^+$. |
| 19 | 3,5-dimethoxy-N-{1-[(2-oxo-1,2,3,4-tetrahydroquinolin-7-yl)methyl]piperidin-4-yl}benzamide | $^1$H NMR (600 MHz, CDCl$_3$, δ): 1.50-1.59 (m, 2H), 1.96-2.04 (m, 2H), 2.11-2.21 (m, 2H), 2.57-2.67 (m, 2H), 2.79-2.86 (m, 2H), 2.89-2.99 (m, 2H), 3.44 (s, 2H), 3.82 (s, 6H), 3.94-4.04 (m, 1H), 5.99 (d, J = 7.8 Hz, 1H), 6.56 (t, J = 2.3 Hz, 1H), 6.73 (s, 1H), 6.86 (d, J = 2.3 Hz, 2H), 6.91 (d, J = 7.3 Hz, 1H), 7.05-7.12 (m, 1H), 7.63 (s, 1H); ESI/APCI MS m/z 424 [M + H]$^+$. |
| 20 | N-{1-[(2-oxo-1,2,3,4-tetrahydroquinolin-7-yl)methyl]piperidin-4-yl}-4-(trifluoromethyl)benzamide | $^1$H NMR (600 MHz, CDCl$_3$, δ): 1.52-1.62 (m, 2H), 2.00-2.05 (m, 2H), 2.13-2.19 (m, 2H), 2.60-2.64 (m, 2H), 2.83-2.89 (m, 2H), 2.94 (t, J = 7.6 Hz, 2H), 3.45 (s, 2H), 4.03 (d, J = 7.8 Hz, 1H), 6.18 (brs, 1H), 6.75 (s, 1H), 6.91 (d, J = 7.8 Hz, 1H), 7.10 (d, J = 7.8 Hz, 1H), 7.69 (d, J = 8.3 Hz, 2H), 7.72 (brs, 1H), 7.88 (d, J = 8.3 Hz, 2H); ESI/APCI MS m/z 432 [M + H]$^+$. |
| 21 | N-{1-[(2-oxo-1,2,3,4-tetrahydroquinolin-7-yl)methyl]piperidin-4-yl}-4-(trifluoromethoxy)benzamide | $^1$H NMR (600 MHz, CDCl$_3$, δ): 1.50-1.59 (m, 2H), 1.96-2.01 (m, 2H), 2.10-2.16 (m, 2H), 2.58-2.61 (m, 2H), 2.80-2.84 (m, 2H), 2.91 (t, J = 7.6 Hz, 2H), 3.42 (s, 2H), 3.96-4.00 (m, 1H), 6.00 (d, J = 8.3 Hz, 1H), 6.70 (s, 1H), 6.88 (d, J = 6.0 Hz, 1H), 7.07 (d, J = 7.8 Hz, 1H), 7.19-7.26 (m, 2H), 7.53 (s, 1H), 7.77 (d, J = 8.7 Hz, 2H); ESI/APCI MS m/z 448 [M + H]$^+$. |
| 22 | 4-cyano-N-{1-[(2-oxo-1,2,3,4-tetrahydroquinolin-7-yl)methyl]piperidin-4-yl}benzamide | $^1$H NMR (600 MHz, CDCl$_3$, δ): 1.60-1.67 (m, 2H), 1.96-2.03 (m, 2H), 2.12-2.18 (m, 2H), 2.59-2.63 (m, 2H), 2.84-2.91 (m, 2H), 2.94 (t, J = 7.6 Hz, 2H), 3.44 (s, 2H), 4.00-4.07 (m, 1H), 6.50 (d, J = 8.3 Hz, 1H), 6.78 (s, 1H), 6.89 (d, J = 6.0 Hz, 1H), 7.10 (d, J = 7.8 Hz, 1H), 7.72 (d, J = 8.7 Hz, 2H), 7.91 (d, J = 8.7 Hz, 2H), 8.11 (brs, 1H); ESI/APCI MS m/z 389 [M + H]$^+$. |
| 23 | N-{1-[(2-oxo-1,2,3,4-tetrahydroquinolin-7-yl)methyl]piperidin-4-yl}benzamide | $^1$H NMR (600 MHz, CDCl$_3$, δ): 1.51-1.61 (m, 2H), 1.98-2.07 (m, 2H), 2.12-2.22 (m, 2H), 2.57-2.68 (m, 2H), 2.80-2.87 (m, 2H), 2.91-2.99 (m, 2H), 3.45 (s, 2H), 3.97-4.06 (m, 1H), 6.03 (d, J = 7.8 Hz, 1H), 6.74 (s, 1H), 6.91 (d, J = 7.3 Hz, 1H), 7.09 (d, J = 7.8 Hz, 1H), 7.38-7.46 (m, 2H), 7.46-7.51 (m, 1H), 7.68-7.78 (m, 3H); ESI/APCI MS m/z 364 [M + H]$^+$. |
| 24 | 2-(4-fluorophenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.28-1.39 (m, 2H), 1.78-1.90 (m, 2H), 2.03-2.11 (m, 2H), 2.57-2.64 (m, 2H), 2.66-2.76 (m, 2H), 2.88-2.98 (m, 2H), 3.38 (s, 2H), 3.49 (s, 2H), 3.73-3.84 (m, 1H), 5.19-5.26 (m, 1H), 6.68 (s, 1H), 6.87 (d, J = 7.3 Hz, 1H), 6.99-7.05 (m, 2H), 7.07 (d, J = 7.3 Hz, 1H), 7.17-7.23 (m, 2H), 7.54 (brs, 1H); ESI/APCI MS m/z 396 [M + H]$^+$. |
| 25 | 2-(3-methoxyphenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.28-1.38 (m, 2H), 1.79-1.88 (m, 2H), 2.01-2.13 (m, 2H), 2.58-2.66 (m, 2H), 2.67-2.77 (m, 2H), 2.90-2.99 (m, 2H), 3.38 (s, 2H), 3.53 (s, 2H), 3.73-3.83 (m, 1H), 3.81 (s, 3H), 5.24-5.32 (m, 1H), 6.69 (s, 1H), 6.73-6.92 (m, 4H), 7.08 (d, J = 7.8 Hz, 1H), 7.22-7.29 (m, 1H), 7.64 (brs, 1H); ESI/APCI MS m/z 408 [M + H]$^+$. |
| 26 | 2-(4-methoxyphenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.24-1.34 (m, 2H), 1.82 (dd, J = 12.6, 3.4 Hz, 2H), 2.00-2.09 (m, 2H), 2.56-2.64 (m, 2H), 2.64-2.76 (m, 2H), 2.92 (t, J = 7.6 Hz, 2H), 3.36 (s, 2H), 3.48 (s, 2H), 3.73-3.82 (m, 4H), 5.23 (d, J = 8.3 Hz, 1H), 6.69 (s, 1H), 6.83-6.88 (m, 3H), 7.06 (d, J = 7.8 Hz, 1H), 7.10-7.15 (m, 2H), 7.94 (s, 1H); ESI/APCI MS m/z 408 [M + H]$^+$. |

TABLE 1-continued

| Example No. | Name of compound | Physical property data |
|---|---|---|
| 27 | N-{1-[(2-oxo-1,2,3,4-tetrahydroquinolin-7-yl)methyl]piperidin-4-yl}-2,2-diphenylacetamide | $^1$H NMR (600 MHz, CDCl$_3$, δ): 1.31-1.41 (m, 2H), 1.85-1.92 (m, 2H), 2.07 (t, J = 10.8 Hz, 2H), 2.57-2.66 (m, 2H), 2.66-2.77 (m, 2H), 2.92 (t, J = 7.6 Hz, 2H), 3.37 (s, 2H), 3.83-3.90 (m, 1H), 4.89 (s, 1H), 5.53 (d, J = 7.8 Hz, 1H), 6.71 (s, 1H), 6.86 (d, J = 7.3 Hz, 1H), 7.06 (d, J = 7.3 Hz, 1H), 7.18-7.27 (m, 6H), 7.27-7.38 (m, 4H), 8.09 (s, 1H); ESI/APCI MS m/z 454 [M + H]$^+$. |
| 28 | 4-chloro-3-fluoro-N-{1-[(2-oxo-1,2,3,4-tetrahydroquinolin-7-yl)methyl]piperidin-4-yl}benzamide | $^1$H NMR (600 MHz, CDCl$_3$, δ): 1.55-1.66 (m, 2H), 1.95-2.03 (m, 2H), 2.09-2.18 (m, 2H), 2.59-2.67 (m, 2H), 2.82-2.90 (m, 2H), 2.92-2.97 (m, 2H), 3.44 (s, 2H), 3.96-4.06 (m, 1H), 6.38 (d, J = 7.3 Hz, 1H), 6.78 (s, 1H), 6.89 (d, J = 6.4 Hz, 1H), 7.09 (d, J = 7.3 Hz, 1H), 7.40-7.48 (m, 1H), 7.50-7.56 (m, 1H), 7.65 (dd, J = 9.6, 1.8 Hz, 1H), 8.02 (brs, 1H); ESI/APCI MS m/z 416 [M + H]$^+$. |
| 29 | 3-bromo-N-{1-[(2-oxo-1,2,3,4-tetrahydroquinolin-7-yl)methyl]piperidin-4-yl}benzamide | $^1$H NMR (600 MHz, CDCl$_3$, δ): 1.56-1.67 (m, 2H), 1.95-2.03 (m, 2H), 2.10-2.19 (m, 2H), 2.59-2.67 (m, 2H), 2.82-2.90 (m, 2H), 2.91-2.97 (m, 2H), 3.44 (s, 2H), 3.97-4.05 (m, 1H), 6.36 (d, J = 7.3 Hz, 1H), 6.78 (s, 1H), 6.89 (d, J = 7.3 Hz, 1H), 7.05-7.12 (m, 1H), 7.30 (t, J = 7.8 Hz, 1H), 7.58-7.63 (m, 1H), 7.72 (d, J = 7.8 Hz, 1H), 7.94 (s, 1H), 8.09 (brs, 1H); ESI/APCI MS m/z 442 [M + H]$^+$. |
| 30 | 3-fluoro-5-methoxy-N-{1-[(2-oxo-1,2,3,4-tetrahydroquinolin-7-yl)methyl]piperidin-4-yl}benzamide | $^1$H NMR (600 MHz, CDCl$_3$, δ): 1.50-1.60 (m, 2H), 1.96-2.04 (m, 2H), 2.12-2.20 (m, 2H), 2.60-2.65 (m, 2H), 2.80-2.88 (m, 2H), 2.91-2.99 (m, 2H), 3.44 (s, 2H), 3.83 (s, 3H), 3.94-4.02 (m, 1H), 5.96 (d, J = 7.8 Hz, 1H), 6.69-6.76 (m, 2H), 6.91 (d, J = 7.8 Hz, 1H), 6.99 (d, J = 8.7 Hz, 1H), 7.06-7.13 (m, 2H), 7.65 (brs, 1H); ESI/APCI MS m/z 412 [M + H]$^+$. |

Example 31

Synthesis of 3-chloro-4-fluoro-N-{1-[(2-oxo-1,2,3,4-tetrahydroquinolin-7-yl)methyl]piperidin-4-yl}benzamide To a DMF (2.50 mL) solution of the compound (250 mg) obtained in Step 1-6, 3-chloro-4-fluoro benzoic acid (191 mg), Et$_3$N (320 μL), HOBt.H$_2$O (222 mg) and EDC.HCl (222 mg) were added and the mixture was stirred at room temperature for three days. To the reaction mixture, a saturated aqueous NaHCO$_3$ solution was added and the solution was extracted four times with CHCl$_3$. The combined organic layers were dried over Na$_2$SO$_4$ and concentrated under reduced pressure. The residue was purified by column chromatography [(silica gel 60 N, mobile phase: MeOH/CHCl$_3$=0/100 to 10/90; v/v) and (Chromatorex NH, mobile phase: CHCl$_3$) in this order]. To the residue, IPA was added at room temperature and the mixture was stirred for one hour. A precipitate was obtained by filtration and washed with IPA and hexane to obtain the titled compound (263 mg, a colorless solid).

$^1$H NMR (600 MHz, CDCl$_3$, δ): 1.53-1.64 (m, 2H), 1.96-2.04 (m, 2H), 2.10-2.20 (m, 2H), 2.58-2.67 (m, 2H), 2.80-2.90 (m, 2H), 2.94 (t, J=7.6 Hz, 2H), 3.45 (s, 2H), 3.93-4.04 (m, 1H), 6.18 (brs, 1H), 6.77 (s, 1H), 6.90 (d, J=7.3 Hz, 1H), 7.10 (d, J=7.8 Hz, 1H), 7.18 (t, J=8.7 Hz, 1H), 7.67 (ddd, J=8.6, 4.5, 2.1 Hz, 1H), 7.83-7.95 (m, 2H); ESI/APCI MS m/z 416 [M+H]$^+$.

The compounds of Examples 32 to 47 were obtained in the same process as in Example 31.

TABLE 2

| Example No. | Name of compound | Physical property data |
|---|---|---|
| 32 | 3-acetyl-N-{1-[(2-oxo-1,2,3,4-tetrahydroquinolin-7-yl)methyl]piperidin-4-yl}benzamide | $^1$H NMR (600 MHz, CDCl$_3$, δ): 1.54-1.64 (m, 2H), 1.97-2.06 (m, 2H), 2.11-2.21 (m, 2H), 2.58-2.68 (m, 5H), 2.81-2.90 (m, 2H), 2.94 (t, J = 7.6 Hz, 2H), 3.45 (s, 2H), 3.96-4.10 (m, 1H), 6.20 (d, J = 8.3 Hz, 1H), 6.75 (s, 1 H), 6.92 (d, J = 7.8 Hz, 1H), 7.07-7.14 (m, 1H), 7.49-7.59 (m, 1H), 7.74 (brs, 1H), 8.01 (d, J = 7.8 Hz, 1H), 8.07 (d, J = 7.3 Hz, 1H), 8.31 (s, 1H); ESI/APCI MS m/z 406 [M + H]$^+$. |
| 33 | 3,4,5-trifluoro-N-{1-[(2-oxo-1,2,3,4-tetrahydroquinolin-7-yl)methyl]piperidin-4-yl}benzamide | $^1$H NMR (600 MHz, CDCl$_3$, δ): 1.52-1.63 (m, 2H), 1.96-2.01 (m, 2H), 2.10-2.19 (m, 2H), 2.58-2.67 (m, 2H), 2.81-2.90 (m, 2H), 2.95 (t, J = 7.6 Hz, 2H), 3.44 (s, 2H), 3.92-4.05 (m, 1H), 6.16 (brs, 1H), 6.75 (s, 1H), 6.90 (d, J = 7.3 Hz, 1H), 7.10 (d, J = 7.8 Hz, 1H), 7.46 (t, J = 7.1 Hz, 2H), 7.74 (brs, 1H); ESI/APCI MS m/z 418 [M + H]$^+$. |
| 34 | 3-ethoxy-N-{1-[(2-oxo-1,2,3,4-tetrahydroquinolin-7-yl)methyl]piperidin-4-yl}benzamide | $^1$H NMR (600 MHz, CDCl$_3$, δ): 1.41 (t, J = 6.9 Hz, 3H), 1.50-1.59 (m, 2H), 2.01-2.04 (m, 2H), 2.16-2.18 (m, 2H), 2.59-2.66 (m, 2H), 2.83-2.86 (m, 2H), 2.94 (t, J = 7.6 Hz, 2H), 3.44 (s, 2H), 3.95-4.03 (m, 1H), 4.07 (q, J = 6.9 Hz, 2H), 5.98-6.05 (m, 1H), 6.74 (brs, 1H), 6.91 (d, J = 7.8 Hz, 1H), 7.01 (dd, J = 8.5, 2.1 Hz, 1H), 7.09 (d, J = 7.8 Hz, 1H), 7.23-7.27 (m, 1H), 7.28-7.34 (m, 2H), 7.60 (brs, 1H); ESI/APCI MS m/z 408 [M + H]$^+$. |
| 35 | 4-fluoro-3-methoxy-N-{1-[(2-oxo-1,2,3,4-tetrahydroquinolin-7-yl)methyl]piperidin-4-yl}benzamide | $^1$H NMR (600 MHz, CDCl$_3$, δ): 1.55-1.63 (m, 2H), 2.03-2.05 (m, 2H), 2.14-2.23 (m, 2H), 2.61-2.68 (m, 2H), 2.84-2.91 (m, 2H), 2.96 (t, J = 7.6 Hz, 2H), 3.47 (brs, 2H), 3.95 (s, 3H), 3.98-4.05 (m, 1H), 6.07 (brs, 1H), 6.78 (brs, 1H), 6.93 (d, J = 7.3 Hz, 1H), |

TABLE 2-continued

| Example No. | Name of compound | Physical property data |
|---|---|---|
| 36 | 3-chloro-5-fluoro-N-{1-[(2-oxo-1,2,3,4-tetrahydroquinolin-7-yl)methyl]piperidin-4-yl}benzamide | 7.06-7.15 (m, 2H), 7.22 (brs, 1H), 7.53 (d, J = 7.3 Hz, 1H), 7.73 (brs, 1H); ESI/APCI MS m/z 412 [M + H]⁺. <br> $^1$H NMR (600 MHz, CDCl$_3$, δ): 1.54-1.64 (m, 2H), 1.99-2.04 (m, 2H), 2.15-2.18 (m, 2H), 2.58-2.67 (m, 2H), 2.82-2.90 (m, 2H), 2.92-2.99 (m, 2H), 3.45 (s, 2H), 3.95-4.04 (m, 1H), 6.24 (brs, 1H), 6.76 (s, 1H), 6.90 (d, J = 7.3 Hz, 1H), 7.10 (d, J = 7.3 Hz, 1H), 7.19-7.22 (m, 1H), 7.42 (d, J = 7.3 Hz, 1H), 7.55 (s, 1H), 7.81 (brs, 1H); ESI/APCI MS m/z 416 [M + H]⁺. |
| 37 | 3-cyano-N-{1-[(2-oxo-1,2,3,4-tetrahydroquinolin-7-yl)methyl]piperidin-4-yl}benzamide | $^1$H NMR (600 MHz, CDCl$_3$, δ): 1.58-1.69 (m, 2H), 2.00-2.05 (m, 2H), 2.16-2.19 (m, 2H), 2.59-2.69 (m, 2H), 2.88-2.92 (m, 2H), 2.95 (t, J = 7.6 Hz, 2H), 3.45 (s, 2H), 3.97-4.09 (m, 1H), 6.53 (brs, 1H), 6.79 (s, 1H), 6.89 (d, J = 7.8 Hz, 1H), 7.10 (d, J = 7.8 Hz, 1H), 7.56 (t, J = 7.8 Hz, 1H), 7.76 (d, J = 7.8 Hz, 1H), 8.05-8.06 (m, 2H), 8.15 (s, 1H); ESI/APCI MS m/z 389 [M + H]⁺. |
| 38 | 5-chloro-N-{1-[(2-oxo-1,2,3,4-tetrahydroquinolin-7-yl)methyl]piperidin-4-yl}pyridine-3-carboxamide | $^1$H NMR (600 MHz, CDCl$_3$, δ): 1.64-1.76 (m, 2H), 1.91-2.03 (m, 2H), 2.09-2.16 (m, 2H), 2.59-2.68 (m, 2H), 2.87-2.92 (m, 2H), 2.94 (t, J = 7.6 Hz, 2H), 3.44 (s, 2H), 4.02-4.12 (m, 1H), 6.83-6.91 (m, 2H), 7.07-7.11 (m, 1H), 7.13 (brs, 1H), 8.25 (s, 1H), 8.66 (d, J = 2.8 Hz, 1H), 8.70 (brs, 1H), 8.96 (s, 1H); ESI/APCI MS m/z 399 [M + H]⁺. |
| 39 | 3-chloro-5-methoxy-N-{1-[(2-oxo-1,2,3,4-tetrahydroquinolin-7-yl)methyl]piperidin-4-yl}benzamide | $^1$H NMR (600 MHz, CDCl$_3$, δ): 1.52-1.65 (m, 2H), 1.94-2.03 (m, 2H), 2.11-2.18 (m, 2H), 2.60-2.66 (m, 2H), 2.82-2.88 (m, 2H), 2.91-2.98 (m, 2H), 3.44 (s, 2H), 3.83 (s, 3H), 3.96-4.03 (m, 1H), 6.21-6.28 (m, 1H), 6.77 (s, 1H), 6.90 (d, J = 7.8 Hz, 1H), 7.00 (d, J = 2.3 Hz, 1H), 7.09 (d, J = 7.3 Hz, 1H), 7.22-7.26 (m, 1H), 7.30 (s, 1H), 7.90 (brs, 1H); ESI/APCI MS m/z 428 [M + H]⁺. |
| 40 | 2-(3-fluorophenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.31-1.40 (m, 2H), 1.81-1.87 (m, 2H), 2.02-2.10 (m, 2H), 2.58-2.63 (m, 2H), 2.68-2.78 (m, 2H), 2.92 (t, J = 7.6 Hz, 2H), 3.38 (s, 2H), 3.52 (s, 2H), 3.75-3.82 (m, 1H), 5.37 (d, J = 8.3 Hz, 1H), 6.70 (s, 1H), 6.86 (d, J = 7.3 Hz, 1H), 6.95-7.03 (m, 3H), 7.07 (d, J = 7.8 Hz, 1H), 7.27-7.32 (m, 1H), 7.89 (brs, 1H); ESI/APCI MS m/z 396 [M + H]⁺. |
| 41 | 2-(2-methoxyphenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.24-1.33 (m, 2H), 1.77-1.85 (m, 2H), 2.01-2.10 (m, 2H), 2.55-2.63 (m, 2H), 2.64-2.73 (m, 2H), 2.92 (t, J = 7.3 Hz, 2H), 3.37 (s, 2H), 3.51 (s, 2H), 3.70-3.79 (m, 1H), 3.83 (s, 3H), 5.53-5.60 (m, 1H), 6.67 (s, 1H), 6.85-6.89 (m, 2H), 6.91-6.94 (m, 1H), 7.07 (d, J = 7.8 Hz, 1H), 7.20 (dd, J = 7.3, 1.8 Hz, 1H), 7.23-7.28 (m, 1H), 7.55 (s, 1H); ESI/APCI MS m/z 408 [M + H]⁺. |
| 42 | 2-(3,4-difluorophenyl)-N-{1-[(2-oxo-1,2,3,4-tetrahydroquinolin-7-yl)methyl]piperidin-4-yl}acetamide- | $^1$H NMR (600 MHz, CDCl$_3$, δ): 1.33-1.43 (m, 2H), 1.83-1.88 (m, 2H), 2.04-2.11 (m, 2H), 2.59-2.63 (m, 2H), 2.75 (brs, 2H), 2.93 (t, J = 7.6 Hz, 2H), 3.39 (brs, 2H), 3.45-3.48 (m, 2H), 3.76-3.81 (m, 1H), 5.39 (brs, 1H), 6.71 (brs, 1H), 6.87 (d, J = 7.3 Hz, 1H), 6.95-6.98 (m, 1H), 7.06-7.12 (m, 3H), 7.63 (brs, 1H); ESI/APCI MS m/z 414 [M + H]⁺. |
| 43 | 4-chloro-3-methyl-N-{1-[(2-oxo-1,2,3,4-tetrahydroquinolin-7-yl)methyl]piperidin-4-yl}benzamide | $^1$H NMR (600 MHz, CDCl$_3$, δ): 1.50-1.61 (m, 2H), 1.96-2.04 (m, 2H), 2.12-2.20 (m, 2H), 2.41 (s, 3H), 2.58-2.65 (m, 2H), 2.81-2.88 (m, 2H), 2.92-2.97 (m, 2H), 3.44 (s, 2H), 3.95-4.04 (m, 1H), 6.07 (d, J = 7.8 Hz, 1H), 6.75 (s, 1H), 6.88-6.93 (m, 1H), 7.09 (d, J = 7.8 Hz, 1H), 7.34-7.39 (m, 1H), 7.49 (dd, J = 8.0, 2.1 Hz, 1H), 7.64 (d, J = 1.8 Hz, 1H), 7.74 (brs, 1H); ESI/APCI MS m/z 412 [M + H]⁺. |
| 44 | 2-(2-fluorophenyl)-N-{1-[(2-oxo-1,2,3,4-tetrahydroquinolin-7-yl)methyl]piperidin-4-yl}acetamide | $^1$H NMR (600 MHz, CDCl$_3$, δ): 1.28-1.43 (m, 2H), 1.79-1.90 (m, 2H), 2.02-2.13 (m, 2H), 2.53-2.65 (m, 2H), 2.65-2.75 (m, 2H), 2.83-3.00 (m, 2H), 3.38 (s, 2H), 3.54 (s, 2H), 3.74-3.82 (m, 1H), 5.34 (d, J = 7.8 Hz, 1H), 6.68 (s, 1H) 6.85-6 88 (m, 1H), 7.03-7.08 (m, 2H), 7.10-7.13 (m, 1H), 7.24-7.30 (m, 2H), 7.56 (brs, 1H); ESI/APCI MS m/z 396 [M + H]⁺. |
| 45 | 2-(4-chlorophenyl)-2-methyl-N-{1-[(2-oxo-1,2,3,4-tetrahydroquinolin-7-yl)methyl]piperidin-4-yl}propanamide | $^1$H NMR (600 MHz, CDCl$_3$, δ): 1.21-1.30 (m, 2H), 1.52 (s, 6H), 1.76-1.83 (m, 2H), 2.01-2.10 (m, 2H), 2.56-2.63 (m, 2H), 2.69 (m, 2H), 2.88-2.96 (m, 2H), 3.36 (s, 2H), 3.68-3.77 (m, 1H), 4.95 (d, J = 7.8 Hz, 1H), 6.67 (s, 1H), 6.86 (d, J = 6.0 Hz, 1H), 7.04-7.09 (m, 1H), 7.22-7.28 (m, 2H), 7.28-7.33 (m, 2H), 7.68 (s, 1H); ESI/APCI MS m/z 440 [M + H]⁺. |
| 46 | 2-(3-chloro-4-fluorophenoxy)-N-{1-[(2-oxo-1,2,3,4-tetrahydroquinolin-7-yl)methyl]piperidin-4-yl}acetamide | $^1$H NMR (600 MHz, CDCl$_3$, δ): 1.45-1.55 (m, 2H), 1.87-1.96 (m, 2H), 2.08-2.17 (m, 2H), 2.59-2.66 (m, 2H), 2.74-2.82 (m, 2H), 2.91-2.98 (m, 2H), 3.42 (s, 2H), 3.86-3.94 (m, 1H), 4.41 (s, 2H), 6.34 (d, J = 7.8 Hz, 1H), 6.71 (s, 1H), 6.75-6.79 (m, 1H), 6.88-6.92 (m, 1H), 6.97 (dd, J = 6.0, 3.2 Hz, 1H), 7.09 (d, J = 8.3 Hz, 2H), 7.66 (brs, 1H); ESI/APCI MS m/z 446 [M + H]⁺. |
| 47 | 2-(3-chlorophenoxy)-N-{1-[(2-oxo-1,2,3,4-tetrahydroquinolin-7-yl)methyl]piperidin-4-yl}acetamide | $^1$H NMR (600 MHz, CDCl$_3$, δ): 1.45-1.55 (m, 2H), 1.88-1.96 (m, 2H), 2.07-2.17 (m, 2H), 2.56-2.66 (m, 2H), 2.73-2.84 (m, 2H), 2.87-2.99 (m, 2H), 3.42 (s, 2H), 3.84-3.96 (m, 1H), 4.44 (s, 2H), 6.36 (d, J = 7.8 Hz, 1H), 6.71 (s, 1H), 6.79 (dd, J = 8.3, 2.3 Hz, |

TABLE 2-continued

| Example No. | Name of compound | Physical property data |
|---|---|---|

1H), 6.90 (d, J = 7.8 Hz, 1H), 6.93 (d, J = 2.3 Hz, 1H), 6.99-7.03 (m, 1H), 7.09 (d, J = 7.3 Hz, 1H), 7.21-7.25 (m, 1H), 7.53 (brs, 1H); ESI/APCI MS m/z 428 [M + H]$^+$.

Example 48

Synthesis of 3-chloro-4-fluoro-N-{1-[(1-methyl-2-oxo-1,2,3,4-tetrahydroquinolin-7-yl)methyl]piperidin-4-yl}benzamide Step 48-1: To a DMF (20 mL) solution of the compound (1.25 g) obtained in Step 1-3, NaH (0.29 g) was added under ice cooling and the mixture was stirred for 30 minutes. To the mixture was added MeI (1.12 g) and the mixture was stirred at room temperature for 12 hours. After water was added, the reaction mixture was extracted three times with EtOAc. The combined organic layers were washed with water and brine, dried over MgSO$_4$ and concentrated under reduced pressure. The residue was purified by column chromatography (silica gel 60 N, mobile phase: EtOAc/hexane=30/70 to 50/50; v/v) to obtain 1-methyl-2-oxo-1,2,3,4-tetrahydroquinolin-7-carbonitrile (0.94 g, a colorless solid).

$^1$H NMR (600 MHz, CDCl$_3$, δ): 2.64-2.73 (m, 2H), 2.92-3.04 (m, 2H), 3.37 (s, 3H), 7.21-7.23 (m, 1H), 7.26-7.29 (m, 1H), 7.31-7.34 (m, 1H); EI MS m/z 186 [M]$^+$.

Step 48-2: From the compound (0.92 g) obtained in Step 48-1, 1-methyl-2-oxo-1,2,3,4-tetrahydroquinoline-7-carbaldehyde (0.93 g, light yellow oil) was obtained in the same process as in Step 1-4.

$^1$H NMR (600 MHz, CDCl$_3$, δ): 2.69-2.75 (m, 2H), 3.00-3.06 (m, 2H), 3.45 (s, 3H), 7.35-7.40 (m, 1H), 7.51-7.53 (m, 1H), 7.54-7.57 (m, 1H), 10.02 (s, 1H); EI MS m/z 189 [M]$^+$.

Step 48-3: To a CHCl$_3$ solution (20 mL) of the compound (0.93 g) obtained in Step 48-2, tert-butyl piperidin-4-ylcarbamate (0.82 g) and AcOH (0.27 g), NaBH(OAc)$_3$ (1.30 g) was added at room temperature and the mixture was stirred at room temperature for 12 hours. After a saturated aqueous NaHCO$_3$ solution was added, a water layer and an organic layer were separated. The water layer was extracted three times with CHCl$_3$. The combined organic layers were dried over Na$_2$SO$_4$ and concentrated under reduced pressure. The residue was purified by column chromatography (Chromatorex NH, mobile phase: EtOAc/hexane=50/50; v/v) to obtain tert-butyl {1-[(1-methyl-2-oxo-1,2,3,4-tetrahydroquinolin-7-yl)methyl]piperidin-4-yl}carbamate (0.78 g, colorless amorphous).

$^1$H NMR (600 MHz, CDCl$_3$, δ): 1.37-1.44 (m, 2H), 1.45 (s, 9H), 1.84-1.97 (m, 2H), 2.07-2.13 (m, 2H), 2.60-2.68 (m, 2H), 2.75-2.84 (m, 2H), 2.85-2.91 (m, 2H), 3.36 (s, 3H), 3.42-3.55 (m, 3H), 4.44 (brs, 1H), 6.91-6.98 (m, 2H), 7.09 (d, J=7.3 Hz, 1H); ESI/APCI MS m/z 374 [M+H]$^+$.

Step 48-4: From the compound (0.77 g) obtained in Step 48-3, 7-[(4-aminopiperidin-1-yl)methyl]-1-methyl-3,4-dihydroquinolin-2(1H)-one (0.57 g, a colorless solid) was obtained in the same process as in Step 1-6.

$^1$H NMR (600 MHz, CDCl$_3$, δ): 1.33-1.45 (m, 2H), 1.76-1.82 (m, 2H), 2.00-2.07 (m, 2H), 2.58-2.67 (m, 2H), 2.66-2.71 (m, 1H), 2.79-2.85 (m, 2H), 2.86-2.90 (m, 2H), 3.37 (s, 3H), 3.48 (s, 2H), 6.95 (d, J=7.8 Hz, 1H), 6.98 (s, 1H), 7.09 (d, J=7.3 Hz, 1H); ESI/APCI MS m/z 274 [M+H]$^+$.

Step 48-5: From the compound (200 mg) obtained in Step 48-4 and 3-chloro-4-fluorobenzoic acid (141 mg), the titled compound (183 mg, a colorless solid) was obtained in the same process as in Example 31.

$^1$H NMR (600 MHz, CDCl$_3$, δ): 1.51-1.58 (m, 2H), 1.98-2.05 (m, 2H), 2.18 (t, J=10.8 Hz, 2H), 2.60-2.68 (m, 2H), 2.83-2.91 (m, 4H), 3.36 (s, 3H), 3.50 (s, 2H), 3.94-4.02 (m, 1H), 5.89 (d, J=7.8 Hz, 1H), 6.95 (d, J=7.3 Hz, 1H), 6.96-6.99 (m, 1H), 7.09 (d, J=7.3 Hz, 1H), 7.18 (t, J=8.7 Hz, 1H), 7.63 (ddd, J=8.6, 4.5, 2.1 Hz, 1H), 7.81 (dd, J=6.9, 2.3 Hz, 1H); ESI/APCI MS m/z 430 [M+H]$^+$.

Example 49

Synthesis of 3-chloro-4-fluoro-N-({1-[(2-oxo-1,2,3,4-tetrahydroquinolin-7-yl)methyl]piperidin-4-yl}methyl)benzamide Step 49-1: From the compound (0.87 g) obtained in Step 1-4 and tert-butyl (piperidin-4-ylmethyl)carbamate (0.88 g), tert-butyl ({1-[(2-oxo-1,2,3,4-tetrahydroquinolin-7-yl)methyl]piperidin-4-yl}methyl)carbamate (0.68 g, a colorless solid) was obtained in the same process as in Step 48-3.

$^1$H NMR (600 MHz, CDCl$_3$, δ): 1.20-1.31 (m, 2H), 1.43 (s, 9H), 1.43-1.45 (m, 1H), 1.61-1.67 (m, 2H), 1.88-1.98 (m, 2H), 2.60-2.67 (m, 2H), 2.83-2.90 (m, 2H), 2.90-2.98 (m, 2H), 2.99-3.05 (m, 2H), 3.42 (s, 2H), 4.56-4.63 (m, 1H), 6.73 (s, 1H), 6.91 (d, J=7.8 Hz, 1H), 7.09 (d, J=7.3 Hz, 1H), 7.86 (s, 1H); ESI/APCI MS m/z 374 [M+H]$^+$.

Step 49-2: From the compound (0.66 g) obtained in Step 49-1, 7-{[4-(aminomethyl)piperidin-1-yl]methyl}-3,4-dihydroquinolin-2(1H)-one (0.35 g, a colorless amorphous) was obtained in the same process as in Step 1-6.

$^1$H NMR (600 MHz, CDCl$_3$, δ): 1.17-1.30 (m, 2H), 1.27-1.33 (m, 1H), 1.66-1.73 (m, 2H), 1.90-1.97 (m, 2H), 2.56-2.60 (m, 2H), 2.61-2.66 (m, 2H), 2.85-2.92 (m, 2H), 2.92-2.97 (m, 2H), 3.42 (s, 2H), 6.76 (s, 1H), 6.92 (d, J=7.3 Hz, 1H), 7.09 (d, J=7.8 Hz, 1H), 8.16 (brs, 1H); ESI/APCI MS m/z 274 [M+H]$^+$.

Step 49-3: From the compound (211 mg) obtained in Step 49-2 and 3-chloro-4-fluorobenzoic acid (145 mg), the titled compound (120 mg, a colorless solid) was obtained in the same process as in Example 31.

$^1$H NMR (600 MHz, CDCl$_3$, δ): 1.29-1.40 (m, 2H), 1.59-1.67 (m, 1H), 1.68-1.74 (m, 2H), 1.92-2.00 (m, 2H), 2.58-2.65 (m, 2H), 2.86-2.91 (m, 2H), 2.91-2.96 (m, 2H), 3.30-3.37 (m, 2H), 3.42 (s, 2H), 6.07-6.13 (m, 1H), 6.70 (s, 1H), 6.90 (d, J=7.3 Hz, 1H), 7.08 (d, J=7.3 Hz, 1H), 7.18 (t, J=8.7 Hz, 1H), 7.45 (brs, 1H), 7.64 (ddd, J=8.4, 4.5, 2.3 Hz, 1H), 7.82 (dd, J=7.1, 2.1 Hz, 1H); ESI/APCI MS m/z 430 [M+H]$^+$.

Example 50

Synthesis of 3-methoxy-N-{1-[2-(2-oxo-1,2,3,4-tetrahydroquinolin-7-yl)ethyl]piperidin-4-yl}benzamide Step 50-1: A mixture of Ph$_3$PCH$_2$OMe.Br (4.97 g) including NaNH$_2$ in THF (20 mL) was stirred under ice cooling for 10 minutes. To the mixture, a THF (80 mL) solution of the compound (1.00 g) obtained in Step 1-4 was slowly added dropwise. After completion of the dropwise addition, the mixture was stirred at room temperature for 4 hours. To the reaction mixture, a saturated aqueous NaHCO$_3$ solution was added and the solution was extracted once with EtOAc and twice with CHCl$_3$. The combined organic layers were washed with brine, dried over MgSO$_4$ and concentrated under reduced pressure. The residue was purified by column chromatography (silica gel 60 N, mobile phase: EtOAc/hexane=20/80 to 40/60; v/v) to obtain 7-(2-methoxyethenyl)-3,4-dihydroquinolin-2(1H)-one (0.60 g, a colorless solid).

$^1$H NMR (600 MHz, CDCl$_3$, δ): 2.48-2.76 (m, 2H), 2.79-3.07 (m, 2H), 3.59-3.84 (m, 3H), 5.10-7.18 (m, 5H), 8.17-8.76 (m, 1H); ESI/APCI MS m/z 204 [M+H]$^+$.

Step 50-2: To a THF (11.8 mL) solution of the compound (590 mg) obtained in Step 50-1, concentrated HCl (8.9 mL) was added under ice cooling and the mixture was stirred at the same temperature for one hour. To the reaction mixture, a saturated K$_2$CO$_3$ was added and the solution was extracted with CHCl$_3$. The organic layer was dried over MgSO$_4$ and concentrated under reduced pressure to obtain (2-oxo-1,2,3,4-tetrahydroquinolin-7-yl)acetaldehyde (0.51 g, colorless amorphous).

$^1$H NMR (600 MHz, CDCl$_3$, δ): 2.60-2.70 (m, 2H), 2.91-3.01 (m, 2H), 3.57-3.76 (m, 2H), 6.58-7.20 (m, 3H), 9.72-9.77 (m, 1H); EI MS m/z 189 [M]$^+$.

Step 50-3: To a DMF (780 mL) suspension of tert-butyl 4-aminopiperidine-1-carboxylate (78.0 g) and 3-methoxybenzoic acid (65.2 g), Et$_3$N (130 mL), HOBt.H$_2$O (71.7 g) and EDC.HCl (82.8 g) were added and the mixture was stirred at room temperature for 12 hours. H$_2$O (1.56 L) was added and the mixture was stirred in a water bath for 1.5 hours. The precipitation was filtrated to obtain tert-butyl 4-[(3-methoxybenzoyl)amino]piperidine-1-carboxylate (126 g, a colorless solid substance). To an EtOAc (900 mL) suspension of the compound obtained in the above process, 4 M HCl/EtOAc solution (900 mL) was added and the mixture was stirred at room temperature for 4 hours. The reaction solution was concentrated under reduced pressure, and thereafter, CHCl$_3$ (2.00 L) and 2 M aqueous NaOH solution (1.00 L) were added to the residue and the mixture was stirred for 15 minutes. A water layer was separated from an organic layer and thereafter extracted twice with CHCl$_3$ (800 mL). The combined organic layers were dried over Na$_2$SO$_4$ and concentrated under reduced pressure to obtain 3-methoxy-N-piperidin-4-ylbenzamide (87.8 g, a light yellow solid).

$^1$H NMR (200 MHz, CDCl$_3$, δ): 1.30-1.52 (m, 2H), 1.97-2.12 (m, 2H), 2.75 (dt, J=12.0, 2.4 Hz, 2H), 3.11 (dt, J=12.8, 3.5 Hz, 2H), 3.85 (s, 3H), 3.96-4.18 (m, 1H), 6.00 (d, J=7.9 Hz, 1H), 6.98-7.07 (m, 1H), 7.21-7.38 (m, 3H); ESI MS m/z 235, [M+H]$^+$.

Step 50-4: From the compound (0.51 g) obtained in Step 50-2 and the compound (0.57 g) obtained in Step 50-3, the titled compound (0.22 g, a colorless solid) was obtained in the same process as in Step 48-3.

$^1$H NMR (600 MHz, CDCl$_3$, δ): 1.50-1.62 (m, 2H), 2.00-2.11 (m, 2H), 2.19-2.27 (m, 2H), 2.54-2.65 (m, 4H), 2.72-2.78 (m, 2H), 2.88-2.99 (m, 4H), 3.84 (s, 3H), 3.96-4.06 (m, 1H), 5.96 (d, J=7.8 Hz, 1H), 6.59 (s, 1H), 6.79-6.86 (m, 1H), 7.02 (dd, J=8.3, 1.8 Hz, 1H), 7.07 (d, J=7.8 Hz, 1H), 7.22-7.28 (m, 1H), 7.29-7.36 (m, 2H), 7.80 (s, 1H); ESI/APCI MS m/z 408 [M+H]$^+$.

Example 51

Synthesis of 3-chloro-4-fluoro-N-{1-[1-(2-oxo-1,2,3,4-tetrahydroquinolin-7-yl)ethyl]piperidin-4-yl}benzamide Step 51-1: To a THF solution (150 mL) of the compound (1.25 g) obtained in Step 1-4, a 3 M MeMgBr Et$_2$O solution was added and the mixture was stirred at room temperature for one hour. To the reaction mixture, a saturated aqueous NH$_4$Cl solution was added and the mixture was stirred for one hour and then an organic layer was separated. The water layer was extracted three times with CHCl$_3$. The combined organic layers were dried over MgSO$_4$ and concentrated under reduced pressure. Thereafter, IPE was added to the residue and the mixture was stirred for 10 minutes. The precipitation was filtrated to obtain 7-(1-hydroxyethyl)-3,4-dihydroquinolin-2(1H)-one (1.02 g, a light yellow solid).

$^1$H NMR (600 MHz, CDCl$_3$, δ): 1.48 (d, J=6.4 Hz, 3H), 2.59-2.67 (m, 2H), 2.91-3.01 (m, 2H), 4.81-4.91 (m, 1H), 6.76-6.79 (m, 1H), 6.96-7.00 (m, 1H), 7.13-7.16 (m, 1H), 7.57 (brs, 1H); ESI/APCI MS m/z 192 [M+H]$^+$.

Step 51-2: To a CHCl$_3$ (120 mL) solution of the compound (1.00 g) obtained in Step 51-1, MnO$_2$ (13.6 g) was added and the mixture was stirred at room temperature for 4 hours. The reaction mixture was filtrated through a pad of Celite and the filtrate was concentrated under reduced pressure. The residue was purified by column chromatography (silica gel 60 N, mobile phase MeOH/CHCl$_3$=0/100 to 10/90; v/v) to obtain 7-acetyl-3,4-dihydroquinolin-2(1H)-one (0.58 g, a colorless solid).

$^1$H NMR (600 MHz, CDCl$_3$, δ): 2.56-2.62 (m, 3H), 2.62-2.72 (m, 2H), 2.99-3.09 (m, 2H), 7.18-7.32 (m, 1H), 7.34-7.40 (m, 1H), 7.51-7.65 (m, 1H), 8.18 (brs, 1H); ESI/APCI MS m/z 190 [M+H]$^+$.

Step 51-3: To a CHCl$_3$ (350 mL) solution of tert-butyl 4-aminopiperidine-1-carboxylate (35.0 g), Et$_3$N (122 mL) and 3-chloro-4-fluorobenzoyl chloride (37.1 g) were added under ice cooling and the mixture was stirred at the same temperature for 1.5 hours. To the reaction mixture, a saturated aqueous NaHCO$_3$ solution was added and the solution was extracted three times with CHCl$_3$. The combined organic layers were dried over MgSO$_4$ and concentrated under reduced pressure to obtain tert-butyl 4-[(3-chloro-4-fluorobenzoyl)amino]piperidine-1-carboxylate (62.0 g). To an EtOAc (300 mL) suspension of the compound obtained, a 4 M HCl/EtOAc solution (300 mL) was added and the mixture was stirred at room temperature for 4 hours. The reaction mixture was concentrated under reduced pressure and 1 M aqueous NaOH solution (300 mL) was added to the residue and the solution was extracted three times with CHCl$_3$. The combined organic layers were dried over MgSO$_4$ and concentrated under reduced pressure. The residue was suspended in EtOAc/hexane (200 mL, 1/1; v/v) and the mixture was stirred for one hour. The precipitate was filtrated to obtain 3-chloro-4-fluoro-N-piperidin-4-ylbenzamide (37.7 g, a colorless solid).

$^1$H NMR (200 MHz, CDCl$_3$, δ): 1.30-1.53 (m, 2H), 1.94-2.12 (m, 2H), 2.75 (td, J=12.0, 2.4 Hz, 2H), 3.10-3.14 (m, 2H), 3.93-4.17 (m, 1H), 5.87-6.09 (m, 1H), 7.19 (t, J=8.6 Hz, 1H), 7.59-7.70 (m, 1H), 7.83 (dd, J=7.0, 2.2 Hz, 1H); ESI MS m/z 257, [M+H]$^+$.

Step 51-4: To a MeOH solution (15 mL) of the compound (206 mg) obtained in Step 51-2, the compound (560 mg) obtained in Step 51-3 and AcOH (327 mg), NaBH$_3$CN (274 mg) was added at room temperature and the mixture was refluxed for 12 hours. After the reaction mixture was cooled to room temperature, NaBH$_3$CN (274 mg) was added and the mixture was refluxed for 72 hours. After a saturated aqueous NaHCO$_3$ solution was added, a water layer and an organic layer were separated. The water layer was extracted three times with CHCl$_3$. The combined organic layers were dried over MgSO$_4$ and concentrated under reduced pressure. The residue was purified by column chromatography [(silica gel 60 N, mobile phase: MeOH/CHCl$_3$=0/100 to 20/80; v/v) and (Chromatorex NH, mobile phase MeOH/CHCl$_3$=0/100 to 10/90; v/v) in this order] to obtain the titled compound (7 mg, a colorless solid).

$^1$H NMR (600 MHz, CDCl$_3$, δ): 1.30-1.37 (m, 3H), 1.44-1.64 (m, 2H), 1.89-2.20 (m, 4H), 2.60-2.67 (m, 2H), 2.72-3.07 (m, 2H), 2.90-2.97 (m, 2H), 3.30-3.37 (m, 1H), 3.88-3.98 (m, 1H), 6.10 (d, J=7.3 Hz, 1H), 6.73 (s, 1H), 6.87-6.92 (m, 1H), 7.09 (d, J=7.8 Hz, 1H), 7.18 (t, J=8.5 Hz, 1H), 7.66 (ddd, J=8.7, 4.6, 2.3 Hz, 1H), 7.79 (brs, 1H), 7.85 (dd, J=6.9, 2.3 Hz, 1H); ESI/APCI MS m/z 430 [M+H]$^+$.

Example 52

Synthesis of N-{1-[(8-fluoro-2-oxo-1,2,3,4-tetrahydroquinolin-7-yl)methyl]piperidin-4-yl}-3-methoxybenzamide Step 52-1: To a MeOH (10.0 mL) solution of the compound (1.00 g) obtained in Step 1-4, NaBH$_4$ (216 mg) was added under ice cooling and the mixture stirred at the same temperature for 30 minutes. To the reaction mixture, a saturated aqueous NaHCO$_3$ solution was added and the mixture was concentrated under reduced pressure. Thereafter, H$_2$O was added to the residue and the solution was extracted three times with CHCl$_3$. The combined organic layers were washed with brine, dried over Na$_2$SO$_4$ and concentrated under reduced pressure. The residue was purified by column chromatography (silica gel 60 N, mobile phase: MeOH/CHCl$_3$=0/100 to 10/90; v/v) to obtain 7-(hydroxymethyl)-3,4-dihydroquinolin-2(1H)-one (550 mg, a colorless solid).

$^1$H NMR (600 MHz, CDCl$_3$, δ): 2.56-2.61 (m, 2H), 2.92 (t, J=7.6 Hz, 2H), 4.62 (d, J=6.0 Hz, 2H), 6.76 (s, 1H), 6.94 (d, J=7.8 Hz, 1H), 7.11 (d, J=7.3 Hz, 1H), 7.90 (brs, 1H); ESI/APCI MS m/z 178 [M+H]$^+$.

Step 52-2: To a CHCl$_3$ (30.0 mL) solution, the compound (670 mg) obtained in Step 52-1, Ac$_2$O (536 μL), DMAP (20.0 mg) and Et$_3$N (1.05 mL) were added under ice cooling and the mixture was stirred at room temperature for 45 minutes. To the reaction mixture, a saturated aqueous NaHCO$_3$ solution was added and the solution was extracted three times with CHCl$_3$. The combined organic layers were dried over Na$_2$SO$_4$ and concentrated under reduced pressure. The residue was purified by column chromatography (silica gel 60 N, mobile phase: MeOH/CHCl$_3$=0/100 to 10/90; v/v) to obtain (2-oxo-1,2,3,4-tetrahydroquinolin-7-yl)methyl acetate (767 mg, a light yellow solid).

$^1$H NMR (600 MHz, CDCl$_3$, δ): 2.09 (s, 3H), 2.61-2.65 (m, 2H), 2.96 (t, J=7.6 Hz, 2H), 5.04 (s, 2H), 6.74 (s, 1H), 6.96-6.99 (m, 1H), 7.15 (d, J=7.3 Hz, 1H), 7.72 (brs, 1H); ESI/APCI MS m/z 220 [M+H]$^+$.

Step 52-3: To a CH$_3$CN (22.0 mL) solution of the compound (958 mg) obtained in Step 52-2, 1-fluoro-4-hydroxy-1,4-diazoniabicyclo[2.2.2]octane bistetrafluoro borate (1.91 g) was added and the mixture was stirred at room temperature for three days. After the reaction mixture was concentrated under reduced pressure, the residue was purified by column chromatography (silica gel 60 N, mobile phase: MeOH/CHCl$_3$=0/100 to 10/90; v/v) to obtain solid A and solid B. To a MeOH (2.00 mL) solution of solid A, K$_2$CO$_3$ (69.0 mg) was added and the mixture was stirred at room temperature for 2 hours. To the reaction mixture was added H$_2$O, the mixture was concentrated under reduced pressure and extracted three times with CHCl$_3$. The combined organic layers were washed with brine, dried over Na$_2$SO$_4$ and concentrated under reduced pressure. The residue was purified by column chromatography (silica gel 60 N, mobile phase: MeOH/CHCl$_3$=0/100 to 15/85; v/v) to obtain 8-fluoro-7-(hydroxymethyl)-3,4-dihydroquinolin-2(1H)-one (37.0 mg, a colorless solid).

$^1$H NMR (600 MHz, CDCl$_3$, δ): 2.63-2.66 (m, 2H), 2.98-3.01 (m, 2H), 4.74 (s, 2H), 6.95 (d, J=7.8 Hz, 1H), 7.02 (t, J=7.6 Hz, 1H), 7.53 (brs, 1H); ESI/APCI MS m/z 196 [M+H]$^+$.

In the same manner, from solid B, 6-fluoro-7-(hydroxymethyl)-3,4-dihydroquinolin-2(1H)-one (76.0 mg, a colorless solid substance) was obtained.

$^1$H NMR (600 MHz, CDCl$_3$, δ): 2.60-2.62 (m, 2H), 2.94 (t, J=7.6 Hz, 2H), 4.72 (s, 2H), 6.79 (d, J=6.4 Hz, 1H), 6.88 (d, J=10.1 Hz, 1H), 7.38 (brs, 1H); ESI/APCI MS m/z 196 [M+H]$^+$.

Step 52-4: To a solution of 8-fluoro-7-(hydroxymethyl)-3,4-dihydroquinolin-2(1H)-one (39.0 mg) obtained in Step 52-3 in CHCl$_3$ (6.00 mL) and acetone (6.00 mL), MnO$_2$ (152 mg) was added and the mixture was stirred at room temperature for 2 days. The reaction mixture was filtrated by Celite and the filtrate was concentrated under reduced pressure to obtain 8-fluoro-2-oxo-1,2,3,4-tetrahydroquinoline-7-carbaldehyde (40.0 mg, a colorless solid).

$^1$H NMR (600 MHz, CDCl$_3$, δ): 2.68-2.71 (m, 2H), 3.06-3.09 (m, 2H), 7.09 (d, J=7.8 Hz, 1H), 7.47 (d, J=7.8 Hz, 1H), 7.60 (brs, 1H), 10.29 (s, 1H); ESI/APCI MS m/z 194 [M+H]$^+$.

Step 52-5: From the compound (40.0 mg) obtained in Step 52-4 and 3-methoxy-N-(piperidin-4-yl)benzamide (73.0 mg), a solid was obtained in the same process as in Step 1-5. To the solid obtained, IPA was added at room temperature and the mixture was stirred for one hour. The precipitate was filtrated, washed with IPA and hexane to obtain the titled compound (8.0 mg, a colorless solid).

$^1$H NMR (600 MHz, CDCl$_3$, δ): 1.47-1.60 (m, 2H), 2.00-2.05 (m, 2H), 2.20-2.31 (m, 2H), 2.63-2.67 (m, 2H), 2.87 (brs, 2H), 2.99 (t, J=7.6 Hz, 2H), 3.57 (brs, 2H), 3.84 (s, 3H), 3.99 (brs, 1H), 5.91 (brs, 1H), 6.90-6.98 (m, 2H), 7.02 (dd, J=8.3, 1.8 Hz, 1H), 7.22-7.25 (m, 1H), 7.30-7.33 (m, 2H), 7.51 (brs, 1H); ESI/APCI MS m/z 412 [M+H]$^+$.

Example 53

Synthesis of N-{1-[(6-fluoro-2-oxo-1,2,3,4-tetrahydroquinolin-7-yl)methyl]piperidin-4-yl}-3-methoxybenzamide Step 53-1: From 6-fluoro-7-(hydroxymethyl)-3,4-dihydroquinolin-2(1H)-one (76.0 mg) obtained in Step 52-3, 6-fluoro-2-oxo-1,2,3,4-tetrahydroquinoline-7-carbaldehyde (32.0 mg, a colorless solid) was obtained in the same process as in Step 52-4.

$^1$H NMR (600 MHz, CDCl$_3$, δ): 2.63-2.66 (m, 2H), 3.02-3.05 (m, 2H), 7.03 (d, J=9.6 Hz, 1H), 7.18 (d, J=5.5 Hz, 1H), 7.54 (brs, 1H), 10.30 (s, 1H); ESI/APCI MS m/z 194 [M+H]$^+$.

Step 53-2: From the compound (32.0 mg) obtained in Step 53-1 and 3-methoxy-N-(piperidin-4-yl)benzamide (58.0 mg), the titled compound (38.0 mg, a colorless solid) was obtained in the same process as in Step 52-5.

$^1$H NMR (600 MHz, CDCl$_3$, δ): 1.51-1.62 (m, 2H), 2.00-2.05 (m, 2H), 2.21-2.28 (m, 2H), 2.59-2.63 (m, 2H), 2.81-2.88 (m, 2H), 2.93 (t, J=7.6 Hz, 2H), 3.52 (brs, 2H), 3.84 (s, 3H), 4.00 (brs, 1H), 5.97 (brs, 1H), 6.76 (d, J=5.5 Hz, 1H), 6.86 (d, J=9.6 Hz, 1H), 7.02 (dd, J=8.7, 2.3 Hz, 1H), 7.22-7.26 (m, 1H), 7.30-7.34 (m, 2H), 7.42-7.46 (m, 1H); ESI/APCI MS m/z 412 [M+H]$^+$.

Reference 1: Synthesis of 3-methoxy-N-{1-[(2-oxo-1,2,3,4-tetrahydroquinolin-7-yl)methyl]piperidin-4-yl}benzamide Step R1-1: To a suspension of 7-hydroxy-3,4-dihydroquinolin-2(1H)-one (200 g) in CHCl$_3$ (2.0 L) was added pyridine (212 g) at room temperature over 10 minutes. Tf$_2$O (344 g) was added to the mixture over 35 minutes, keeping the temperature below 10° C. After the mixture was allowed to warm to 15° C. over 1 hour, the reaction mixture was cooled to 0° C. and quenched by addition of water (2.0 L). The organic layer was separated, washed with aqueous saturated KHSO$_4$ and water twice, dried over Na$_2$SO$_4$ and concentrated to obtain 2-oxo-1,2,3,4-tetrahydroquinolin-7-yl trifluoromethanesulfonate as a pale yellow solid (346 g).

$^1$H NMR (200 MHz, CDCl$_3$, δ): 2.63-2.72 (m, 2H), 2.96-3.05 (m, 2H), 6.75 (d, J=2.2 Hz, 1H), 6.90 (dd, J=8.4, 2.2 Hz, 1H), 7.20-7.26 (m, 1H), 8.83 (brs, 1H); ESI/APCI MS m/z 294 [M–H]$^-$.

Step R1-2: The mixture of 2-oxo-1,2,3,4-tetrahydroquinolin-7-yl trifluoromethanesulfonate (338 g), Zn(CN)$_2$ (134 g) and Pd(PPh$_3$)$_4$ (33.5 g) in DMF (3.0 L) was heated at 100° C. for 4 hours and cooled to room temperature. To the mixture, Zn(CN)$_2$ (134 g) and Pd(PPh$_3$)$_4$ (12.7 g) were added and the mixture was stirred at 100° C. for 2 hours. After cooling to 60° C., the reaction mixture was filtrated through a pad of Celite. The filtrate was concentrated to obtain a solid. The solid was washed with EtOAc twice to obtain 2-oxo-1,2,3,4-tetrahydroquinoline-7-carbonitrile as a pale yellow solid (165 g).

$^1$H NMR (600 MHz, DMSO-d$_6$, δ): 2.43-2.45 (m, 2H), 2.90-2.97 (m, 2H), 7.12 (s, 1H), 7.31-7.37 (m, 2H), 10.29 (s, 1H); ESI/APCI MS m/z 171 [M–H]$^-$.

Step R1-3: To a suspension of 2-oxo-1,2,3,4-tetrahydroquinoline-7-carbonitrile (160 g) in HCO$_2$H (1.6 L) was added Raney Nickel Catalyst (slurry in water, 160 g) at room temperature over 30 minutes. The mixture was heated at 100° C. for 2 hours. After cooling to room temperature, the reaction mixture was filtrated through a pad of Celite and washed with HCO$_2$H. The filtrate was concentrated to obtain a solid. The solid was stirred with water (1.3 L) and filtrated to obtain 2-oxo-1,2,3,4-tetrahydroquinoline-7-carbaldehyde as a pale brown solid (156 g).

$^1$H NMR (600 MHz, DMSO-d$_6$, δ): 2.43-2.45 (m, 2H), 2.94 (t, J=7.6 Hz, 2H), 7.30 (s, 1H), 7.38 (d, J=7.3 Hz, 1H), 7.44-7.49 (m, 1H), 9.87 (s, 1H), 10.29 (s, 1H); ESI/APCI MS m/z 176 [M+H]$^+$.

Step R1-4: To a solution of tert-butyl 4-aminopiperidine-1-carboxylate (150 g) and Et$_3$N (209 mL) in IPA (1.0 L) was added 3-methoxybenzoyl chloride (102 mL) over 40 minutes under ice cooling. The mixture was stirred at room temperature for 2 hours. After cooling to 0° C., 12 M aqueous HCl (0.5 L) was added to the mixture over 30 minutes and the mixture was stirred at 50° C. for 1 hour. After cooling to 0° C., 12 M aqueous NaOH (0.5 L) and water (0.4 L) were added over 40 minutes to the reaction mixture. The organic layer was separated and the aqueous layer was extracted with EtOAc. The combined organic layers were washed with brine, dried over MgSO$_4$ and concentrated to obtain 3-methoxy-N-(piperidin-4-yl)benzamide as a light brown solid (160 g).

$^1$H NMR (600 MHz, DMSO-d$_6$, δ): 1.52-1.61 (m, 2H), 1.78-1.86 (m, 2H), 2.71 (td, J=12.3, 2.5 Hz, 2H), 3.06-3.15 (m, 2H), 3.79 (s, 3H), 3.84-4.02 (m, 1H), 7.07 (ddd, J=8.0, 2.5, 0.92 Hz, 1H), 7.33-7.46 (m, 3H), 8.32 (d, J=7.8 Hz, 1H); ESI/APCI MS m/z 235 [M+H]$^+$.

Step R1-5: To a suspension of 2-oxo-1,2,3,4-tetrahydroquinoline-7-carbaldehyde (135 g) in CHCl$_3$ (1.4 L) were added 3-methoxy-N-(piperidin-4-yl)benzamide (190 g) and AcOH (45 mL) at room temperature. The mixture was stirred at room temperature for 2 hours. After cooling to 0° C., NaBH(OAc)$_3$ was added portionwise. The mixture was stirred at room temperature for 19 hours. After cooling to 0° C., 8 M aqueous NaOH (0.5 L) and water (0.5 L) were added to the reaction mixture. The organic layer was separated, washed with water and brine, dried over MgSO$_4$ and concentrated to obtain a colorless solid. The solid was suspended in EtOAc (3.0 L) and the mixture was refluxed for 1 hour and cooled to room temperature. The precipitate was filtrated to obtain a colorless solid. The solid was suspended again in EtOAc (2.4 L), and the mixture was refluxed for 1 hour and cooled to room temperature. The precipitate was filtrated to obtain the titled compound as a colorless solid (229 g).

$^1$H NMR (600 MHz, CDCl$_3$, δ): 1.48-1.62 (m, 2H), 1.94-2.06 (m, 2H), 2.10-2.21 (m, 2H), 2.57-2.67 (m, 2H), 2.78-2.87 (m, 2H), 2.90-2.99 (m, 2H), 3.44 (s, 2H), 3.85 (s, 3H), 3.94-4.05 (m, 1H), 6.01 (d, J=7.8 Hz, 1H), 6.77 (s, 1H), 6.91 (d, J=7.3 Hz, 1H), 7.02 (dd, J=7.6, 2.1 Hz, 1H), 7.09 (d, J=7.8 Hz, 1H), 7.21-7.27 (m, 1H), 7.29-7.35 (m, 2H), 8.00 (s, 1H); ESI/APCI MS m/z 394 [M+H]$^+$.

TABLE 3

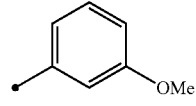

(I)

| Example | A$^1$ | A$^2$ | A$^3$ | R | X | Y | Z | W | Cy | salt |
|---|---|---|---|---|---|---|---|---|---|---|
| 1 | H | H | H | H | CH$_2$ | Bond | Bond | Bond | 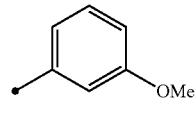 | free |
| 2 | H | H | H | H | CH$_2$ | Bond | Bond | Bond | 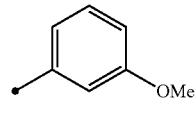 | HCl |

TABLE 3-continued
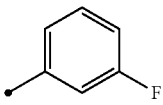
(I)
| Example | A¹ | A² | A³ | R | X | Y | Z | W | Cy | salt |
|---|---|---|---|---|---|---|---|---|---|---|
| 3 | H | H | H | H | CH$_2$ | Bond | Bond | Bond | 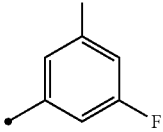 | free |
| 4 | H | H | H | H | CH$_2$ | Bond | Bond | Bond | 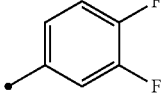 | free |
| 5 | H | H | H | H | CH$_2$ | Bond | Bond | Bond | 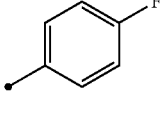 | free |
| 6 | H | H | H | H | CH$_2$ | Bond | Bond | Bond | 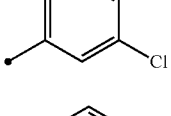 | free |
| 7 | H | H | H | H | CH$_2$ | Bond | Bond | Bond | 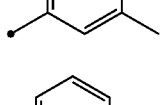 | free |
| 8 | H | H | H | H | CH$_2$ | Bond | Bond | Bond | 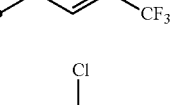 | free |
| 9 | H | H | H | H | CH$_2$ | Bond | Bond | Bond | 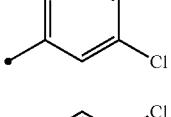 | free |
| 10 | H | H | H | H | CH$_2$ | Bond | Bond | Bond | 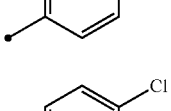 | free |
| 11 | H | H | H | H | CH$_2$ | Bond | Bond | Bond | 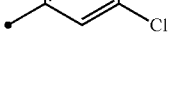 | free |
| 12 | H | H | H | H | CH$_2$ | Bond | Bond | Bond |  | free |

TABLE 3-continued

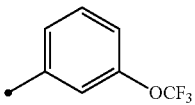

(I)

| Example | A¹ | A² | A³ | R | X | Y | Z | W | Cy | salt |
|---|---|---|---|---|---|---|---|---|---|---|
| 13 | H | H | H | H | CH₂ | Bond | Bond | Bond | 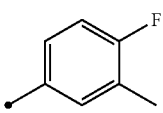 3-OCF₃-phenyl | free |
| 14 | H | H | H | H | CH₂ | Bond | Bond | Bond | 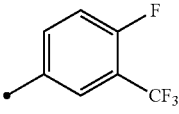 4-F-3-Me-phenyl | free |
| 15 | H | H | H | H | CH₂ | Bond | Bond | Bond | 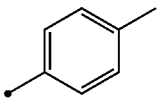 4-F-3-CF₃-phenyl | free |
| 16 | H | H | H | H | CH₂ | Bond | Bond | Bond | 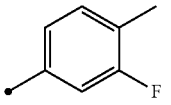 4-Me-phenyl | free |
| 17 | H | H | H | H | CH₂ | Bond | Bond | Bond | 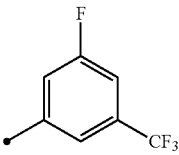 3-F-4-Me-phenyl | free |
| 18 | H | H | H | H | CH₂ | Bond | Bond | Bond | 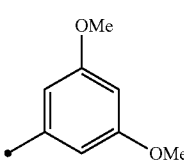 3-F-5-CF₃-phenyl | free |
| 19 | H | H | H | H | CH₂ | Bond | Bond | Bond | 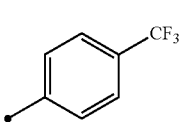 3,5-diOMe-phenyl | free |
| 20 | H | H | H | H | CH₂ | Bond | Bond | Bond | 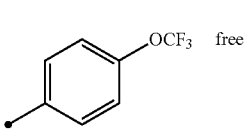 4-CF₃-phenyl | free |
| 21 | H | H | H | H | CH₂ | Bond | Bond | Bond | 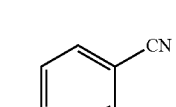 4-OCF₃-phenyl | free |
| 22 | H | H | H | H | CH₂ | Bond | Bond | Bond | 4-CN-phenyl | free |

TABLE 3-continued
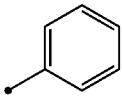
(I)
| Example | A¹ | A² | A³ | R | X | Y | Z | W | Cy | salt |
|---|---|---|---|---|---|---|---|---|---|---|
| 23 | H | H | H | H | CH₂ | Bond | Bond | Bond | 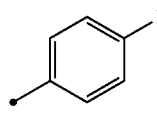 | free |
| 24 | H | H | H | H | CH₂ | Bond | CH₂ | Bond | 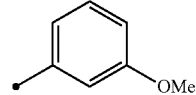 | free |
| 25 | H | H | H | H | CH₂ | Bond | CH₂ | Bond | 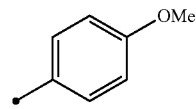 | free |
| 26 | H | H | H | H | CH₂ | Bond | CH₂ | Bond | 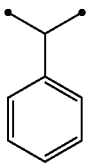 | free |
| 27 | H | H | H | H | CH₂ | Bond | 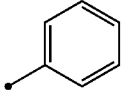 | Bond | 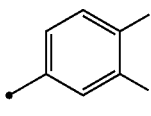 | free |
| 28 | H | H | H | H | CH₂ | Bond | Bond | Bond | 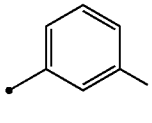 | free |
| 29 | H | H | H | H | CH₂ | Bond | Bond | Bond | 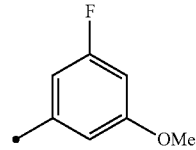 | free |
| 30 | H | H | H | H | CH₂ | Bond | Bond | Bond | 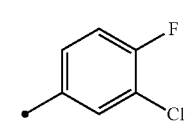 | free |
| 31 | H | H | H | H | CH₂ | Bond | Bond | Bond | 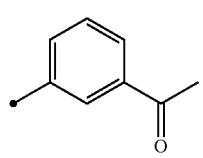 | free |
| 32 | H | H | H | H | CH₂ | Bond | Bond | Bond |  | free |

TABLE 3-continued
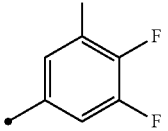
(I)
| Example | A¹ | A² | A³ | R | X | Y | Z | W | Cy | salt |
|---|---|---|---|---|---|---|---|---|---|---|
| 33 | H | H | H | H | CH₂ | Bond | Bond | Bond | 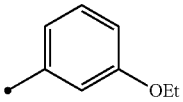 | free |
| 34 | H | H | H | H | CH₂ | Bond | Bond | Bond | 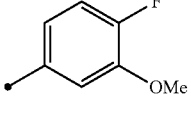 | free |
| 35 | H | H | H | H | CH₂ | Bond | Bond | Bond | 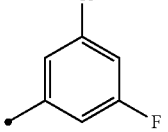 | free |
| 36 | H | H | H | H | CH₂ | Bond | Bond | Bond | 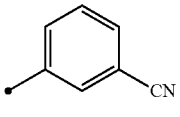 | free |
| 37 | H | H | H | H | CH₂ | Bond | Bond | Bond | 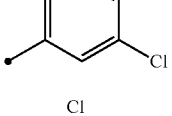 | free |
| 38 | H | H | H | H | CH₂ | Bond | Bond | Bond | 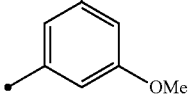 | free |
| 39 | H | H | H | H | CH₂ | Bond | Bond | Bond | 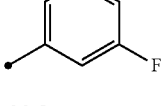 | free |
| 40 | H | H | H | H | CH₂ | Bond | CH₂ | Bond | 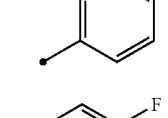 | free |
| 41 | H | H | H | H | CH₂ | Bond | CH₂ | Bond | 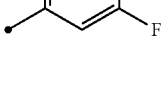 | free |
| 42 | H | H | H | H | CH₂ | Bond | CH₂ | Bond |  | free |

TABLE 3-continued
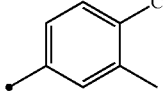
(I)
| Example | A¹ | A² | A³ | R | X | Y | Z | W | Cy | salt |
|---|---|---|---|---|---|---|---|---|---|---|
| 43 | H | H | H | H | CH₂ | Bond | Bond | Bond | 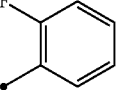 | free |
| 44 | H | H | H | H | CH₂ | Bond | CH₂ | Bond | 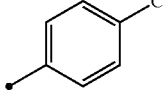 | free |
| 45 | H | H | H | H | CH₂ | Bond | CMe₂ | Bond | 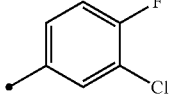 | free |
| 46 | H | H | H | H | CH₂ | Bond | CH₂ | O | 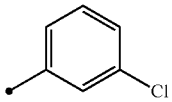 | free |
| 47 | H | H | H | H | CH₂ | Bond | CH₂ | O | 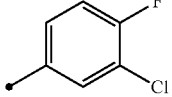 | free |
| 48 | H | H | H | Me | CH₂ | Bond | Bond | Bond | 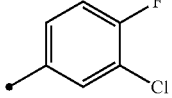 | free |
| 49 | H | H | H | H | CH₂ | CH₂ | Bond | Bond | 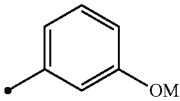 | free |
| 50 | H | H | H | H | CH₂CH₂ | Bond | Bond | Bond | 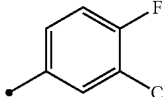 | free |
| 51 | H | H | H | H | CHMe | Bond | Bond | Bond | 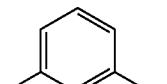 | free |
| 52 | H | H | F | H | CH₂ | Bond | Bond | Bond | 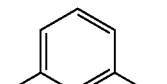 | free |
| 53 | H | F | H | H | CH₂ | Bond | Bond | Bond | 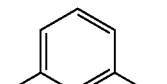 | free |

Example 54

Calcium Evaluation Test for MCH1R

An FDSS assay can measure the intracellular calcium concentration and can evaluate the Gq-coupled receptor activity using the calcium concentration as an index. For example, the assay can determine whether an analyte is an antagonist, an inverse agonist or an agonist for a Gq-coupled receptor. The FDSS6000™ system (Hamamatsu Photonics K.K.) is designed to perform evaluation based on functionality such as measurement of intracellular calcium for high-throughput screening. Intracellular calcium release by activation of a Gq-coupled receptor can be fluorometrically measured by incorporating a calcium indicator (such as Fluo4) into cells. On the other hand, the assay cannot measure the activation of Gi- and Go-coupled receptors, because the activation is not associated with calcium signaling pathways.

Intracellular fluorescence can be rapidly and successively measured in a 96-well microplate or a 384-well microplate using a fluorometric imaging plate reader system. FDSS6000™ can simultaneously measure fluorescence in all wells sensitively, accurately and by seconds. This system is ideal for functional analysis in cells such as monitoring of an intracellular calcium flow generated within several seconds after activation of a Gq-coupled receptor.

Test Method

On the day before the test, cells stably expressing non-endogenous active MCH1R were seeded into a 96-well microplate at $3\times10^4$ cells per well. 100 µL per well of a medium (Dulbecco's modified Eagle medium containing 10% fetal bovine serum, 2 mM glutamine, 1 mM sodium pyruvate and 0.5 mg/mL G418, pH=7.4) was used for culture. On the day of the test, the medium was removed and an assay buffer {Hank's balanced salt solution containing 20 mM HEPES, 0.5 mM probenecid, 0.05 mg/mL amaranth and 0.2% bovine serum albumin (BSA), pH=7.4} containing 2 µM Fluo-4-AM and 0.04% Pluronic F127 was added at 100 µL per well, followed by incubation in a 5% $CO_2$ incubator at 37° C. for 30 minutes. An assay buffer containing each concentration of MCH was added at 50 µL per well, and transient changes in the intracellular calcium concentration induced by MCH were monitored using FDSS6000™ at Ex. 488 nm and Em. 530 nm for 180 seconds. In testing the antagonistic activity of the analyte, MCH was added to a final concentration of 50 nM. An inhibition curve was prepared with various concentrations of the analyte, and the concentration of the analyte inhibiting 50% of the increase in intracellular calcium when 50 nM MCH was added ($IC_{50}$ value) was calculated using data analysis software Origin Ver. 6.

Of the compounds of the present invention, the compounds having an $IC_{50}$ value of 50 nM or less are shown below:
Example Nos. 1, 2, 3, 4, 5, 6, 7, 8, 10, 12, 14, 15, 18, 19, 23, 27, 28, 29, 30, 31, 32, 33, 35, 36, 37, 38, 39, 43, 46, 47, 51 and 53.

Furthermore, $IC_{50}$ values of some compounds of the present invention are shown in Table 4.

TABLE 4

| Example No. | $IC_{50}$ (nM) |
|---|---|
| 2 | 6.22 |
| 3 | 10.9 |
| 5 | 1.50 |
| 7 | 9.08 |
| 8 | 19.2 |

TABLE 4-continued

| Example No. | $IC_{50}$ (nM) |
|---|---|
| 19 | 3.85 |
| 27 | 19.7 |
| 32 | 10.7 |
| 33 | 1.96 |
| 37 | 18.3 |
| 38 | 18.8 |
| 46 | 4.34 |
| 51 | 1.07 |
| 53 | 39.3 |

INDUSTRIAL APPLICABILITY

The compound of the present invention has MCH receptor antagonistic action and used as a prophylactic or therapeutic drug for disease associated with MCH, and more specifically, can be used as a prophylactic or therapeutic drug for depression, anxiety disorders (such as generalized anxiety disorder, posttraumatic stress disorder, panic disorder, obsessive-compulsive disorder or social anxiety disorder), attention deficit disorder, mania, manic-depressive illness, schizophrenia, mood disorders, stress, sleep disorders, attacks, memory impairment, cognitive impairment, dementia, amnesia, delirium, obesity, eating disorder, appetite disorder, hyperphagia, bulimia, cibophobia, diabetes, cardiovascular diseases, hypertension, dyslipidemia, myocardial infarction, movement disorder (such as Parkinson's disease, epilepsy, convulsion or tremor), drug abuse, drug addiction or sexual dysfunction.

The invention claimed is:
1. A compound represented by formula (I), a pharmaceutically acceptable salt or a hydrate thereof:

[Formula 1]

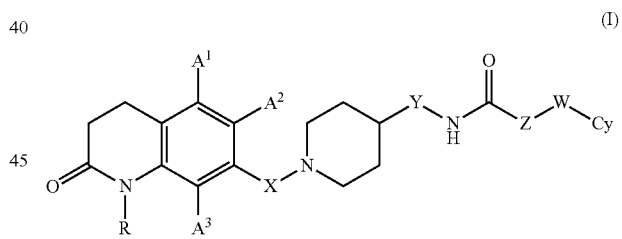

wherein, in the formula (I)
R is a hydrogen atom or a $C_{1-6}$ alkyl group;
$A^1$, $A^2$ and $A^3$, which may be the same or different, are each a hydrogen atom, a halogen atom, a $C_{1-6}$ alkyl group or a $C_{1-6}$ alkoxy group;
X is a $C_{1-6}$ alkylene group;
Y is a bond or a $C_{1-6}$ alkylene group;
Z is a bond or a $C_{1-6}$ alkylene group, wherein the $C_{1-6}$ alkylene group may be substituted with an aryl group;
W is a bond or an oxygen atom; and
Cy is a phenyl group or a pyridyl group, wherein the phenyl group or the pyridyl group may have one to three substituents, which may be the same or different, selected from the group consisting of a halogen atom, a cyano group, a $C_{1-6}$ alkyl group, a $C_{1-6}$ alkoxy group, wherein the $C_{1-6}$ alkyl group or the $C_{1-6}$ alkoxy group may be substituted with one to three halogen atoms, and a $C_{2-6}$ alkanoyl group.

2. The compound, a pharmaceutically acceptable salt or a hydrate thereof according to claim 1, wherein, in the formula (I), R is a hydrogen atom;
$A^1$, $A^2$ and $A^3$ are each a hydrogen atom;
X is a $C_{1-6}$ alkylene group;
Y is a bond;
Z is a bond or a $C_{1-6}$ alkylene group, wherein the $C_{1-6}$ alkylene group may be substituted with an aryl group;
W is a bond or an oxygen atom; and
Cy is a phenyl group or a pyridyl group, wherein the phenyl group or the pyridyl group may have one to three substituents, which may be the same or different, selected from the group consisting of a halogen atom, a cyano group, a $C_{1-6}$ alkyl group, a $C_{1-6}$ alkoxy group, wherein the $C_{1-6}$ alkyl group or the $C_{1-6}$ alkoxy group may be substituted with one to three halogen atoms, and a $C_{2-6}$ alkanoyl group.

3. The compound, a pharmaceutically acceptable salt or a hydrate thereof according to claim 1, wherein, in the formula (I), R is a hydrogen atom;
$A^1$, $A^2$ and $A^3$ are each a hydrogen atom;
X is a methylene group, wherein the methylene group may be substituted with a methyl group;
Y is a bond;
Z is a bond or a methylene group;
W is a bond or an oxygen atom; and
Cy is a phenyl group, wherein the phenyl group may have one to three substituents, which may be the same or different, selected from the group consisting of a halogen atom, a $C_{1-6}$ alkyl group, a $C_{1-6}$ alkoxy group and a $C_{2-6}$ alkanoyl group.

4. The compound, pharmaceutically acceptable salt or a hydrate thereof according to claim 1, wherein the compound represented by the formula (I) is 3-methoxy-N-{1-[(2-oxo-1,2,3,4-tetrahydroquinolin-7-yl)methyl]piperidin-4-yl}benzamide,
3-fluoro-N-{1-[(2-oxo-1,2,3,4-tetrahydroquinolin-7-yl)methyl]piperidin-4-yl}benzamide,
3,5-difluoro-N-{1-[(2-oxo-1,2,3,4-tetrahydroquinolin-7-yl)methyl]piperidin-4-yl}benzamide,
3,4-difluoro-N-{1-[(2-oxo-1,2,3,4-tetrahydroquinolin-7-yl)methyl]piperidin-4-yl}benzamide,
4-fluoro-N-{1-[(2-oxo-1,2,3,4-tetrahydroquinolin-7-yl)methyl]piperidin-4-yl}benzamide,
3-chloro-N-{1-[(2-oxo-1,2,3,4-tetrahydroquinolin-7-yl)methyl]piperidin-4-yl}benzamide,
3-methyl-N-{1-[(2-oxo-1,2,3,4-tetrahydroquinolin-7-yl)methyl]piperidin-4-yl}benzamide,
3,5-dichloro-N-{1-[(2-oxo-1,2,3,4-tetrahydroquinolin-7-yl)methyl]piperidin-4-yl}benzamide,
3,4-dichloro-N-{1-[(2-oxo-1,2,3,4-tetrahydroquinolin-7-yl)methyl]piperidin-4-yl}benzamide,
4-fluoro-3-methyl-N-{1-[(2-oxo-1,2,3,4-tetrahydroquinolin-7-yl)methyl]piperidin-4-yl}benzamide,
4-fluoro-N-{1-[(2-oxo-1,2,3,4-tetrahydroquinolin-7-yl)methyl]piperidin-4-yl}-3-(trifluoromethyl)benzamide,
3-fluoro-N-{1-[(2-oxo-1,2,3,4-tetrahydroquinolin-7-yl)methyl]piperidin-4-yl}-5-(trifluoromethyl)benzamide,
3,5-dimethoxy-N-{1-[(2-oxo-1,2,3,4-tetrahydroquinolin-7-yl)methyl]piperidin-4-yl}benzamide,
N-{1-[(2-oxo-1,2,3,4-tetrahydroquinolin-7-yl)methyl]piperidin-4-yl}benzamide,
N-{1-[(2-oxo-1,2,3,4-tetrahydroquinolin-7-yl)methyl]piperidin-4-yl}-2,2-diphenylacetamide,
4-chloro-3-fluoro-N-{1-[(2-oxo-1,2,3,4-tetrahydroquinolin-7-yl)methyl]piperidin-4-yl}benzamide,
3-bromo-N-{1-[(2-oxo-1,2,3,4-tetrahydroquinolin-7-yl)methyl]piperidin-4-yl}benzamide,
3-fluoro-5-methoxy-N-{1-[(2-oxo-1,2,3,4-tetrahydroquinolin-7-yl)methyl]piperidin-4-yl}benzamide,
3-chloro-4-fluoro-N-{1-[(2-oxo-1,2,3,4-tetrahydroquinolin-7-yl)methyl]piperidin-4-yl}benzamide,
3-acetyl-N-{1-[(2-oxo-1,2,3,4-tetrahydroquinolin-7-yl)methyl]piperidin-4-yl}benzamide,
3,4,5-trifluoro-N-{1-[(2-oxo-1,2,3,4-tetrahydroquinolin-7-yl)methyl]piperidin-4-yl}benzamide,
4-fluoro-3-methoxy-N-{1-[(2-oxo-1,2,3,4-tetrahydroquinolin-7-yl)methyl]piperidin-4-yl}benzamide,
3-chloro-5-fluoro-N-{1-[(2-oxo-1,2,3,4-tetrahydroquinolin-7-yl)methyl]piperidin-4-yl}benzamide,
3-cyano-N-{1-[(2-oxo-1,2,3,4-tetrahydroquinolin-7-yl)methyl]piperidin-4-yl}benzamide,
5-chloro-N-{1-[(2-oxo-1,2,3,4-tetrahydroquinolin-7-yl)methyl]piperidin-4-yl}pyridine-3-carboxamide,
3-chloro-5-methoxy-N-{1-[(2-oxo-1,2,3,4-tetrahydroquinolin-7-yl)methyl]piperidin-4-yl}benzamide,
4-chloro-3-methyl-N-{1-[(2-oxo-1,2,3,4-tetrahydroquinolin-7-yl)methyl]piperidin-4-yl}benzamide,
2-(3-chloro-4-fluorophenoxy)-N-{1-[(2-oxo-1,2,3,4-tetrahydroquinolin-7-yl)methyl]piperidin-4-yl}acetamide,
2-(3-chlorophenoxy)-N-{1-[(2-oxo-1,2,3,4-tetrahydroquinolin-7-yl)methyl]piperidin-4-yl}acetamide,
3-chloro-4-fluoro-N-{1-[1-(2-oxo-1,2,3,4-tetrahydroquinolin-7-yl)ethyl]piperidin-4-yl}benzamide or
N-{1-[(6-fluoro-2-oxo-1,2,3,4-tetrahydroquinolin-7-yl)methyl]piperidin-4-yl}-3-methoxybenzamide.

5. A pharmaceutical composition containing the compound, a pharmaceutically acceptable salt or a hydrate thereof according to claim 1 as an active ingredient, and a pharmaceutically acceptable carrier.

6. The pharmaceutical composition according to claim 5, which is a melanin-concentrating hormone receptor antagonist.

7. A method for treating depression, anxiety disorders (generalized anxiety disorder, posttraumatic stress disorder, panic disorder, obsessive-compulsive disorder or social anxiety disorder), obesity, eating disorder, appetite disorder, hyperphagia, bulimia and cibophobia, comprising administering an effective amount of the compound, a pharmaceutically acceptable salt or a hydrate thereof according to claim 1 to a patient in need thereof.

* * * * *